US010309974B2

(12) United States Patent
Fert-Bober et al.

(10) Patent No.: US 10,309,974 B2
(45) Date of Patent: Jun. 4, 2019

(54) CITRULLINATED PROTEINS: A POST-TRANSLATED MODIFICATION OF MYOCARDIAL PROTEINS AS MARKER OF PHYSIOLOGICAL AND PATHOLOGICAL DISEASE

(71) Applicant: Cedars-Sinai Medical Center, Los Angeles, CA (US)

(72) Inventors: Justyna P. Fert-Bober, Sherman Oaks, CA (US); Jennifer E. Van Eyk, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/814,200

(22) Filed: Nov. 15, 2017

(65) Prior Publication Data

US 2018/0136232 A1    May 17, 2018

Related U.S. Application Data

(63) Continuation-in-part of application No. 15/661,766, filed on Jul. 27, 2017, which is a continuation of application No. 13/885,146, filed as application No. PCT/US2011/060640 on Nov. 14, 2011.

(60) Provisional application No. 61/412,819, filed on Nov. 12, 2010.

(51) Int. Cl.
*G01N 33/53* (2006.01)
*G01N 33/68* (2006.01)
*G01N 33/564* (2006.01)
*C12Q 1/34* (2006.01)

(52) U.S. Cl.
CPC ........... *G01N 33/6893* (2013.01); *C12Q 1/34* (2013.01); *G01N 33/564* (2013.01); *G01N 33/6812* (2013.01); *G01N 33/6848* (2013.01); *G01N 2440/18* (2013.01); *G01N 2800/32* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 8,519,096 B2 | 8/2013 | Ling et al. | |
| 2001/0004168 A1 | 11/2001 | Schwarz | |
| 2001/0041680 A1 | 11/2001 | Schwarz | |
| 2004/0265849 A1 | 12/2004 | Cargill et al. | |
| 2006/0020570 A1 | 9/2006 | Eggenweiler et al. | |
| 2006/0205708 A1 | 9/2006 | Eggenweiler et al. | |
| 2011/0024449 A1 | 10/2011 | Ossetrova | |
| 2011/0244492 A1 | 10/2011 | Ossetrova | |
| 2014/0308676 A1 | 10/2014 | Fert-Bober et al. | |
| 2017/0328915 A1 | 11/2017 | Fert-Bober et al. | |
| 2018/0299467 A1 | 10/2018 | Van Eyk et al. | |

FOREIGN PATENT DOCUMENTS

| | | |
|---|---|---|
| CA | 2817847 A1 | 5/2012 |
| CN | 107923917 A | 4/2018 |
| EP | 2638401 A2 | 9/2013 |
| EP | 2638401 B1 | 2/2017 |
| EP | 3311176 A2 | 4/2018 |
| IN | 201817001039 A | 3/2018 |
| JP | 2007524100 A | 8/2007 |
| JP | 2009510464 A | 3/2009 |
| JP | 2009-155226 A | 7/2009 |
| JP | 2014503795 A | 2/2014 |
| JP | 5701994 B2 | 4/2015 |
| JP | 2018-524575 A | 8/2018 |
| WO | 2009/103988 A1 | 8/2009 |
| WO | 2010/104964 A1 | 9/2010 |
| WO | 2012065176 A2 | 5/2012 |
| WO | 2014/016584 A2 | 1/2014 |
| WO | 2014/037911 A1 | 3/2014 |
| WO | 2016205828 A2 | 12/2016 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Kidd et al., Epitope spreading to citrullinated antigens in mouse models of autoimmune arthritis and demyelination, Arthritis Research & Therapy, vol. 10, No. 5, pp. 1-12. (Year: 2008).*
PCT/US2016/038439 International Search Report and Written Opinion dated Dec. 8, 2016, 11 pages.
PCT/US2011/060640 Written Opinion dated May 8, 2012, 3 pages.
PCT/US2011/060640 International Preliminary Report on Patentability dated May 14, 2013, 4 pages.
EP 11840460.7 Extended Search Report dated Feb. 14, 2014, 10 pages.
Almer et al., Inducible Nitric Oxide Synthase Up-Regulation in Transgenic Mouse Model of Familial Amyotrophic Lateral Sclerosis, Journal of Neurochemistry, 1999, pp. 2415-2425.
Prion 2008 Conference Abstract Book retrieved from http://www.neuroprion.org/resources/pdf_docs/conferences/prion2008/abstract-book-prion2008.pdf on Jan. 24, 2014.
Taub et al., Biomarkers of Heart Failure, Congestive Heart Failure, 2010, vol. 16, pp. S19-S24.
PCT/US2016/038439 International Preliminary Report on Patentability dated Dec. 19, 2017, 7 pages.

*Primary Examiner* — Gary Counts
(74) *Attorney, Agent, or Firm* — Seth D. Levy; Nixon Peabody LLP

(57) ABSTRACT

Disclosed herein are methods for diagnosing cardiovascular disease. The methods comprise detection of citrullinated proteins and/or citrullinated peptides. Also disclosed herein are methods, compositions, and kits for diagnosing and/or treating cardiovascular disease.

20 Claims, 14 Drawing Sheets

Specification includes a Sequence Listing.

(56) References Cited

OTHER PUBLICATIONS

Amador et al., Serum Lactic Dehydrogenase Activity: An Analytical Assessment of Current Assays, Clinical Chemistry, 1963, vol. 9(4), pp. 391-399.

Avasthi et al., Serum Lipid Profile and Lipoprotein Lipase Activity in Patients of Ischaemic Heart Disease, Indian Journal of Clinical BioChemistry, 1992, vol. 7(2), pp. 199-202; Abstract Only.

Backs et al., Control of Cardiac Growth by Histone Acetylation/Deacetylation, Circulation Research, 2006, vol. 98, pp. 15-24.

Chang et al., Citrullination of Fibronectin in Rheumatoid Arthritis Synovial Tissue, Rheumatology, 2005, vol. 44(11), pp. 1374-1382.

Chang et al., Increased PADI4 Expression in Blood and Tissues of Patients with Malignant Tumors, BMC Cancer, 2009, vol. 9(1), pp. 40.

Gabriel et al., The Epidemiology of Rheumatoid Arthritis in Rochester, Minnesota, 1955-1985, Arthritis and Rheumatology, 1999, vol. 42(3), pp. 415-420.

Giles et al., Left Ventricular Structure and Function in Patients with Rheumatoid Arthritis, as Assessed by Cardiac Magnetic Resonance Imaging, Arthritis and Rheumatism, 2010, vol. 62, pp. 940-951.

Hermansson et al., Mass Spectrometric Analysis of Rheumatoid Arthritic Synovial Tissue Identifies Specific Citrullination Sites on Fibrinogen, Proteomics, 2010.

Holm et al., Specific Modification of Peptide-Bound Citrulline Residues, Analytical Biochemistry, 2006, vol. 352, pp. 68-76.

Inagaki et al., Ca2+-Dependent Deimination-Induced Disassembly of Intermediate Filaments Involves Specific Modification of the Amino-Terminal Head Domain, Journal of Biological Chemistry, 1989, vol. 264, pp. 18119-18127.

Ishida-Yamamoto et al., Sequential Reorganization of Cornified Cell Keratin Filaments Involving Filaggrin-Mediated Compaction and Keratin 1 Deimination, Journal of Investigative Dermatology, 2002, vol. 118(2), pp. 282-287.

Jacquet et al., Identification of Cardiac Myosin-Binding Protein C as a Candidate Biomarker of Myocardial Infarction by Proteomics Analysis, Molecular Cell Proteomics, 2009, vol. 8(12), pp. 2687-2699.

Jaffe et al., Comparative Sensitivity of Cardiac Troponin I and Lactate Dehydrogenase Isoenzymes for Diagnosing Acute Myocardial Infarction, The American Association for Clinical Chemistry, 1996, vol. 42(11), pp. 1770-1776.

Kane et al., Subfraction of Heart Tissue: The "In Sequence" Myofilament Protein Extraction of Myocardial TissueCardiovascular Proteomics, 2007, vol. 357, pp. 87-90.

Kidd et al., Epitope Spreading to Cirullinated Antigens in Mouse Models of Autoimmune Arthritis and Demyelination, Arthritis Research and Therapy, 2008, vol. 10(5), pp. 1-12.

Levy et al., Incidence and Risk of Fatal Myocardial Infarction and Stroke Events in Rheumatoid Arthritis Patients, Clin Exp Rheumatol, 2008, vol. 4, pp. 673-679.

Lofberg et al., Myosin Heavy-Chain Fragments and Cardiac Troponins in the Serum in Rhabdomyolysis, Diagnostic Specificity of New BioChemical Markers, Arch Neurology, 1995, vol. 52(12), pp. 1210-1214; Abstract Only.

Lopez-Longo et al., Association Between Anti-Cyclic Citrullinated Peptide Antibodies and Ischemic Heart Disease in Patients with Rheumatoid Arthritis, Arthritis and Rheumatism, 2009, vol. 61(4), pp. 419-424.

Lundberg et al., Antibodies to Citrullinated α-Enolase Peptide 1 are Specific for Rheumatoid Arthritis and Cross-React with Bacterial Enolase, Arthritis and Rheumatology, 2008, vol. 58(10), pp. 3009-3019.

Makrygiannakis et al., Citrullination is an Inflammation-Dependent Process, Annals of Rheumatic Disease, 2006, vol. 65(9), pp. 1219-1222.

Martinez-Amat et al., Release of α-actin into Serum after Skeletal Muscle Damage, Br J Sports Medicine, 2005, vol. 39, pp. 830-834.

Mastronardi et al., Increased Citrullination of Histone H3 in Multiple Sclerosis Brain and Animal Models of Demyelination: A Role for Tumor Necrosis Factor-Induced Peptidylarginine Deiminase 4 Translocation, Journal of Neuroscience, 2006, vol. 26(44), pp. 11387-11396.

Nadareishvili et al., Cardiovascular, Rheumatologic and Pharmacologic Predictors of Stroke in Patients with Rheumatoid Arthritis, A Nested, Case-Control Study, Arthritis Care and Research, 2008, vol. 59(8), pp. 1090-1096.

Nicholas et al., Immunohistochemical Localization of Citrullinated Proteins in Adult Rat Brain, Journal of Comparative Neurology, 2003, vol. 459, pp. 251-266.

Okamoto et al., Serum Alpha 1-Antichimotrypsin Levels and Cardiovascular Risk Factors in the Japanese Elderly Population, J. Epidemiol., 1998, vol. 8(2), pp. 94-98.

Raptopoulou et al., Anti-Citrullinated Antibodies in the Diagnosis and Prognosis of Rheumatoid Arthritis: Evolving Concepts, Critical Reviews in Clinical Lab Sciences, 2007, vol. 44(4), pp. 339-363.

Shevchenko et al., Mass Spectrometric Sequencing of Proteins from Silver-Stained Polyacrylamide Gels, Analytical Chemistry, 1996, vol. 68(5), pp. 850-858.

Shibata et al., Anti-Cyclic Citrullinated Peptide Antibodies and IL-23p19 in Psoriatic Arthritis, Journal of Dermatological Science, 2009, vol. 53(1), pp. 34-39.

Sihvonen et al., Death Rates and Causes of Death in Patients with Rheumatoid Arthritis: A Population-Based Study, Scandinavian Journal of Rheumatology, 2004, vol. 33(4), pp. 221-227.

Spencer et al., Role of Covalent Modifications of Histones in Regulating Gene Expression, Gene, 1999, vol. 240(1), pp. 1-12.

Stensland et al., Targeted Analysis of Protein Citrullination using Chemical Modification and Tandem Mass Spectrometry, Rapid Communication in Mass Spectrometry, 2009, vol. 23(17), pp. 2754-2762.

Strongin, Laboratory Diagnosis of Viral Infections, Sensetivity, Specificity and Predictive Value of Diagnostic Tests: Definitions and Clinical Applications, 1992, pp. 211-219.

Tarcsa et al., Protein Unfolding by Peptidylarginine Deiminase, Journal of Biological Chemistry, 1996, vol. 271(48), pp. 30709-30716.

Torzewski et al., Animal Models of C-Reactive Protein, Mediators of Inflammation, 2014, vol. 2014, pp. 1-7.

Turesson et al., Severe Extra-Articular Disease Manifestations are Associated with an Increased Risk of First Ever Cardiovascular Events in Patients with Rheumatoid Arthritis, Annals of Rheumatic Disease, 2007, vol. 66(1), pp. 70-75.

Van Der Vekiens et al., Human and Equine Cardiovascular Endocrinology: Beware to Compare, Cardiovascular Endocrinology, 2013, vol. 2(4), pp. 67-76.

Van Gaalen et al., Association between HLA Class II Genes and Autoantibodies to Cyclic Citrullinated Peptides (CCPs) Influences the Severity of Rheumatoid Arthritis, Arthritis and Rheumatology, 2004, vol. 50(7), pp. 2113-2121.

Wolfe et al., The Risk of Myocardial Infarction and Pharmacologic and Nonpharmacologic Myocardial Infarction Predictors in Rheumatoid Arthritis, Arthritis Rheumatism, 2008, vol. 58(9), pp. 2612-2621.

Yamada et al., Citrulline and Anti-Cyclic Citrullinated Peptide Antibodies in Rheumatoid Arthritis, Future Rheumatology, 2006, vol. 1(2), pp. 249-258.

Zhang et al., Proteomic Profiling of the Silkworm Skeletal Muscle Proteins during Larval-Pupal Metamorphosis, Journal of Proteome Research, 2007, vol. 6(6), pp. 2295-2303.

EP 16812648.0 Extended Search Report dated Oct. 19, 2018, 19 pages.

Jang et al., Accumulation of Citrullinated Proteins by Up-Regulated Peptidylarginine Deiminase 2 in Brains of Scrapie-Infecte d Mice, American Journal of Pathology, 2008, vol. 173 (4), pp. 1129-1142.

Jang et al., Peptidylarginine deiminase modulates the physiological roles of enolase via citrullination: links between altered multifunction of enolase and neurodegenerative diseases, Biochemical Journal, 2012, vol. 445 (2), pp. 183-192.

Jang et al., Peptidylarginine deiminase and protein citrullination in prion diseases: Strong evidence of neurodegeneration, Prion, 2013, vol. 7 (1), pp. 42-46.

(56) References Cited

OTHER PUBLICATIONS

Nicholas, Dual immunofluorescence study of citrullinated proteins in Parkinson diseased substantia nigra, Neuroscience Letters, 2011, vol. 495 (1), pp. 26-29.
Turner et al., Biomarkers in amyotrophic lateral sclerosis, Lancet Neurology, 2009, vol. 8 (1), pp. 94-109.
EP 16812648.0 Extended Search Report dated Feb. 13, 2019, 19 pages.
Fert-Bober et al., Citrullination of myofilament proteins in heart failure, Cardiovascular Research, 2015, 108, pp. 232-242.
Choi et al., Abnormal-Accumulation of citrullinated proteins in Scrapie-Infected mouse brain, Alzheimer's & Dementia, The Journal of the Alzheimer's Association, Jul. 2006, vol. 2, Issue 3, Supplemental p. S551.
Ishigami et al., Abnormal Accumulation of Citrullinated Proteins Catalyzed by Peptidylargine Deiminase in Hippocampal Extracts from Patients with Alzheimer's Disease, Journal of Neuroscience Research 80, 2005, pp. 120-128.
Moscarello et al., The Role of Citrullinated Proteins Suggests a Novel Mechanism in the Pathogenesis of Multiple Sclerosis, Neurochem Res, 2007, 32, pp. 251-256.

\* cited by examiner

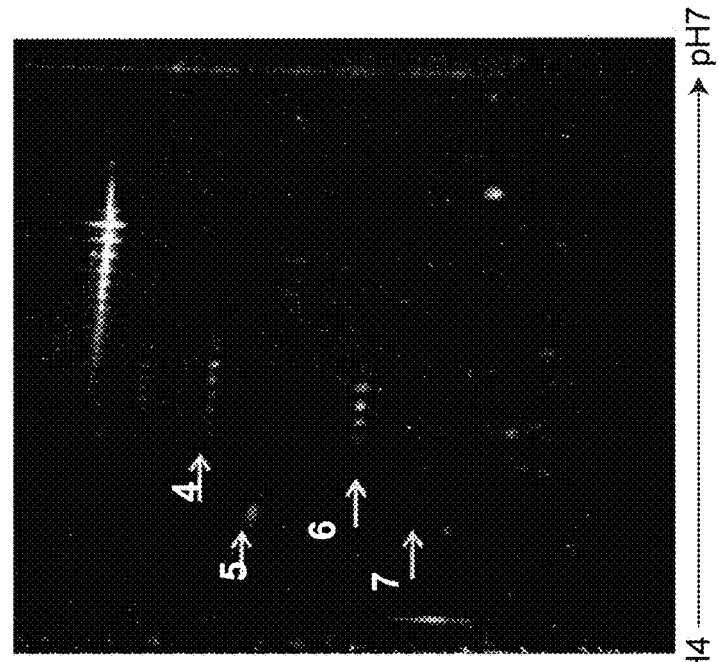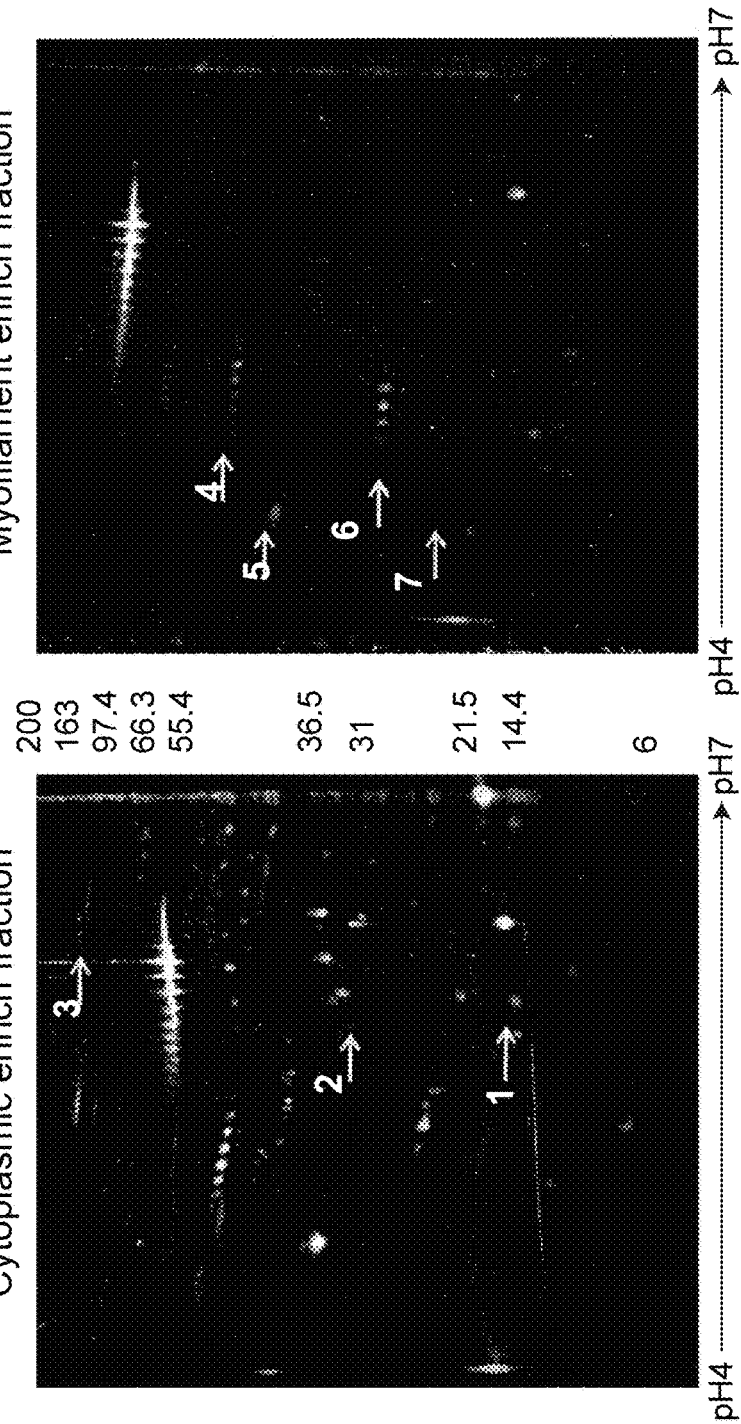

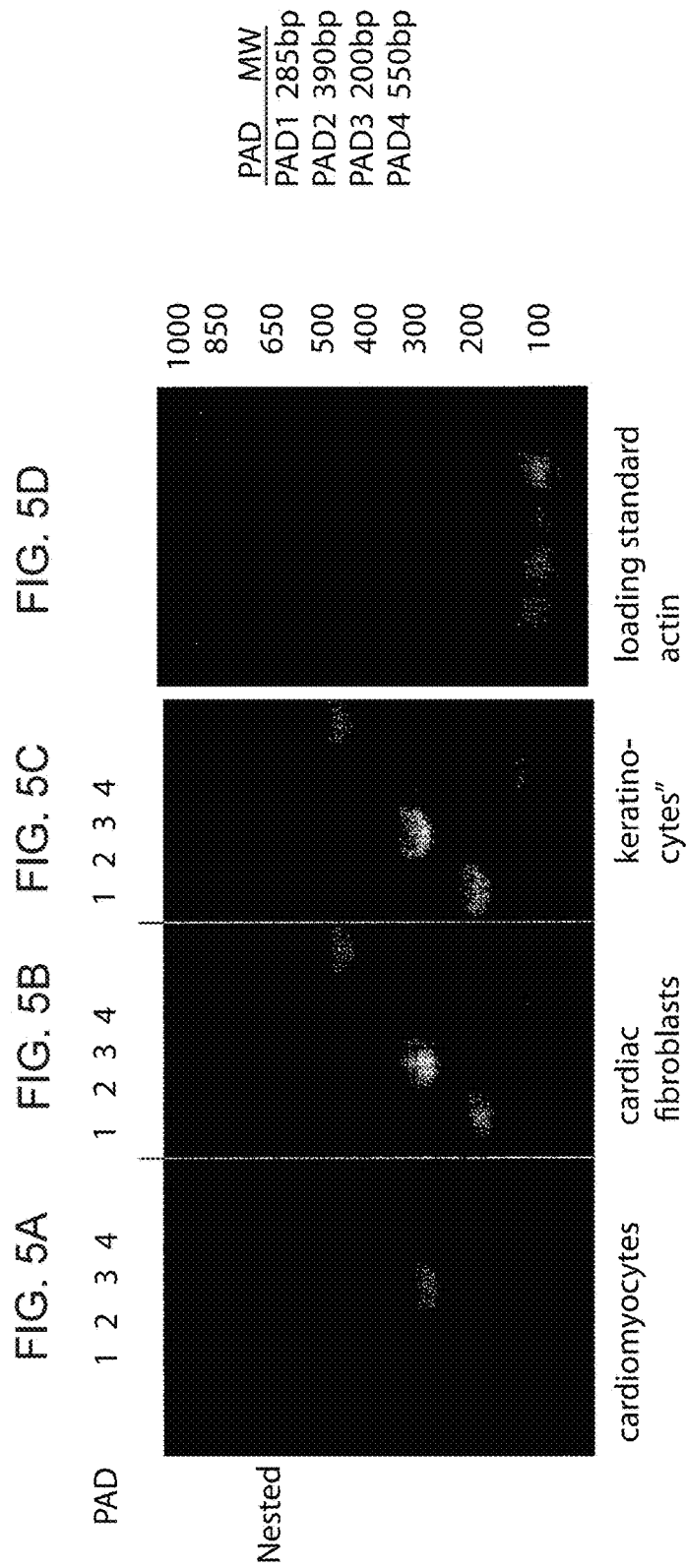

FIG. 7A

| Mouse ID (dots) | ID | TAC day | Sac day | Mouse weight [g] pre | Mouse body weight [g] post | Heart weight [g] | HW/postBW |
|---|---|---|---|---|---|---|---|
| TAC drug 1 * | 72677 | 71516 | 72416 | 30 | 27.7 | 117.4 | (4.238267) |
| TAC drug 2 ** | 72672 | 71516 | 72416 | 34 | 32.2 | 175.7 | (5.456522) |
| TAC2 drug | 72681 | 60416 | 61416 | | 25 | 134.4 | (5.376) |
| TAC p1 | 72686 | 61516 | 62416 | | 29.7 | 165 | (5.555556) |
| TAC p2 | 72678 | 61516 | 62416 | | 27.9 | 168 | 6.021505 |
| TAC p2.2 | 72680 | 61516 | 61416 | | 26.2 | 110 | 4.198473 |
| TAC1 DMSO | 72679 | 60416 | 72416 | 30 | 26.5 | 176.5 | (6.660377) |
| TAC DMSO 1 * | 72674 | 71516 | 62416 | | 28.5 | 192.4 | (6.750877) |
| TAC DMSO | | 61516 | 62416 | | 29.3 | 175 | (5.972696) |
| TAC sham | | 61516 | 61416 | | 25 | 91 | (3.64) |
| sham | | 60416 | 72416 | | 25.5 | 103 | (4.039216) |
| TAC sham | | 71516 | 72416 | 38 | 31.1 | 118.1 | (3.797428) |
| naive | | 71516 | | | 38 | 152.7 | |

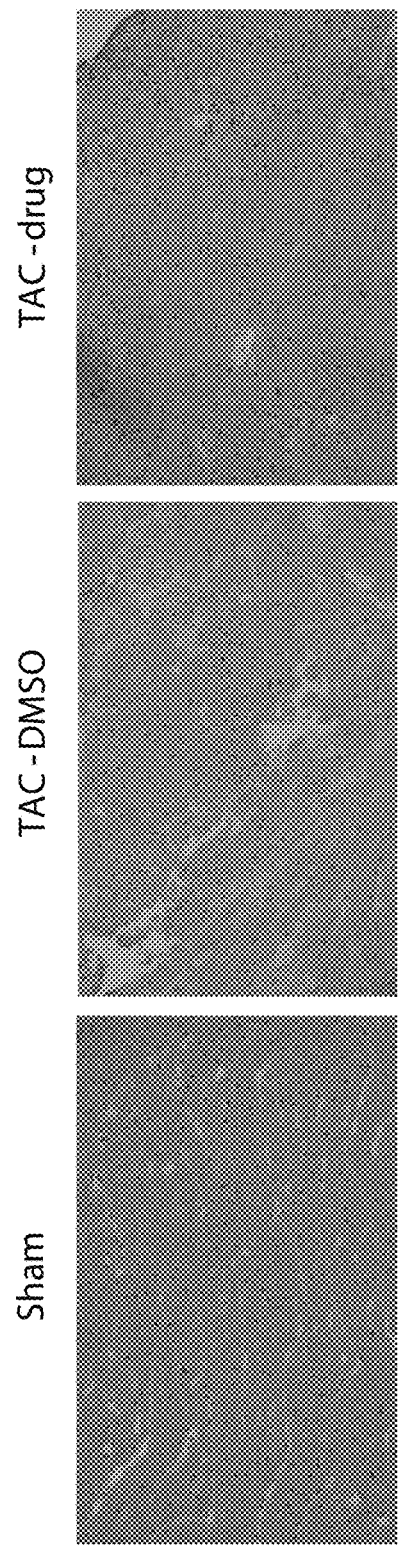

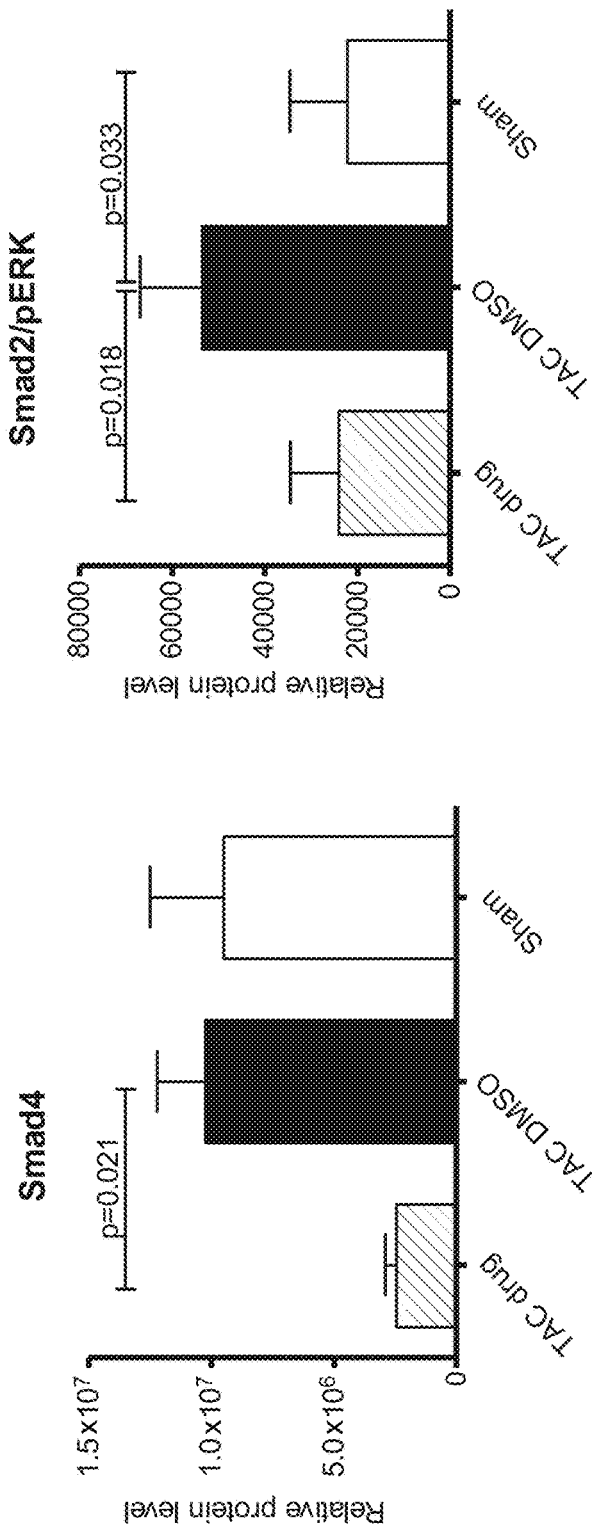

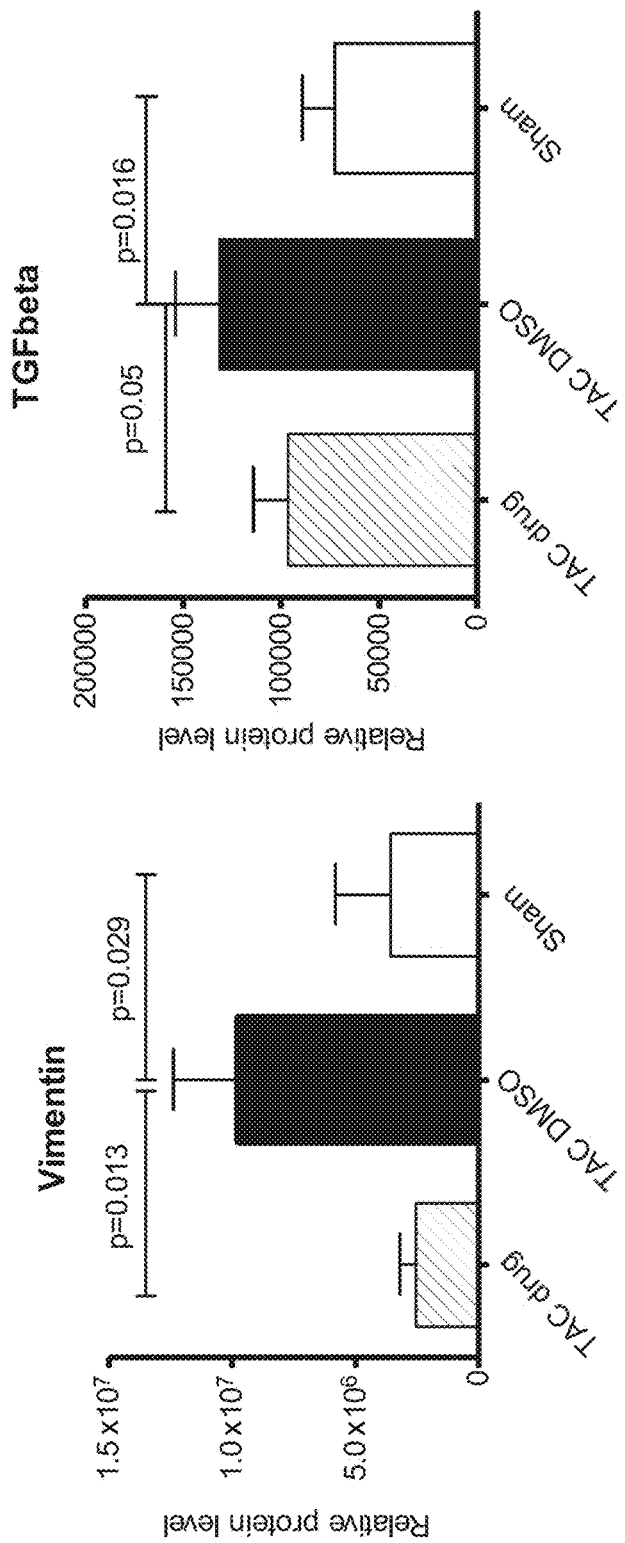

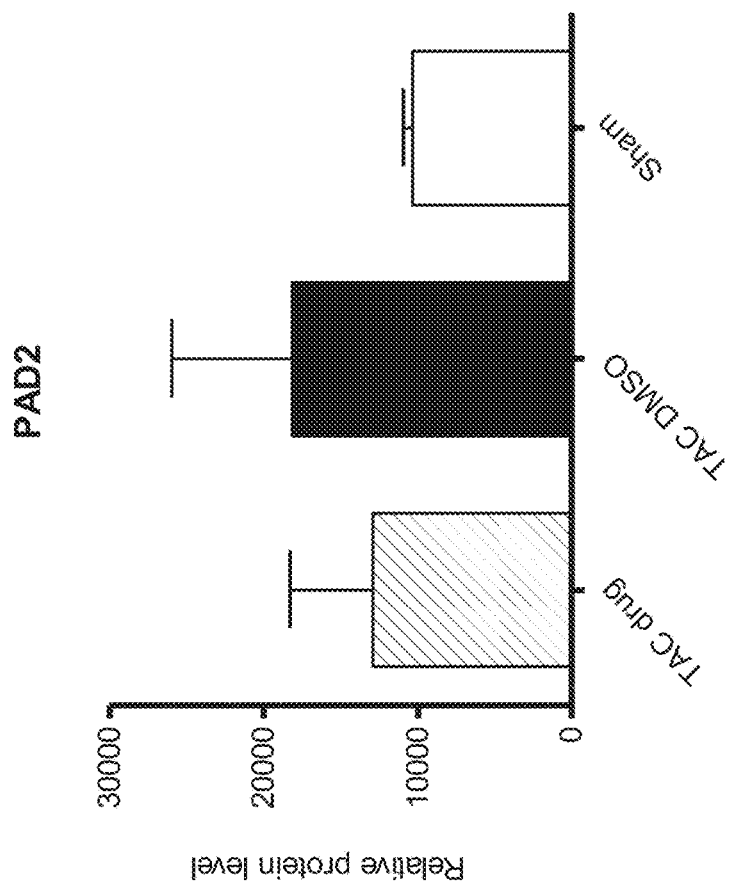

FIG. 9

Table 4. Summary of the seven proteins

| Gel view | MS/MS ID* | Accession Number | Coverage % | Observed pI/MW | Theoretical pI/MW | P <0.05 |
|---|---|---|---|---|---|---|
| 1 | Fatty acid binging protein, heart | P05413 | 63.2 | 6.0/14.500 | 6.29/14.858 | 0.20* |
| 2 | L-lactate dehydrogenase B chain | P07195 | 35.8 | 5.8/36.000 | 5.71/36.638 | 0.13* |
| 3 | Vinculin | P18206 | 4.5 | 6.2/170.00 | 5.83/123.799 | 0.19* |
| 4 | Actin, alpha cardiac | P62736 | 30.1 | 5.5/44.000 | 5.24/42.009 | 0.020 |
| 5 | Tropomyosin | P09493 | 6.2 | 4.6/38.000 | 4.69/32.709 | 0.0020 |
| 6 | Myosin light chain | P08590 | 32 | 5.0/24.000 | 5.03/21.932 | 0.021 |
| 7 | Myosin regulatory light chain 2 | P10916 | 39.8 | 4.9/18.000 | 4.92/18.788 | 0.0018 |

* Not statistical significant

CITRULLINATED PROTEINS: A POST-TRANSLATED MODIFICATION OF MYOCARDIAL PROTEINS AS MARKER OF PHYSIOLOGICAL AND PATHOLOGICAL DISEASE

CROSS-REFERENCE TO RELATED APPLICATIONS

This application is a continuation-in-part of U.S. patent application Ser. No. 15/661,766 filed Jul. 27, 2017, which is a continuation of U.S. patent application Ser. No. 13/885,146 filed Mar. 17, 2014, which is a National Phase of International Application No. PCT/US2011/060640 filed Nov. 14, 2011, which designated the U.S. and that International Application was published under PCT Article 21(2) in English, which also includes a claim of priority under 35 U.S.C. § 119(e) to U.S. Provisional Patent Application No. 61/412,819 filed Nov. 12, 2010, the entirety of each of which are herein incorporated by reference.

STATEMENT REGARDING FEDERALLY SPONSORED RESEARCH OR DEVELOPMENT

This invention was made with government support under Grant Nos. HV028180 and HL063038 awarded by National Institutes of Health. The government has certain rights in the invention.

FIELD OF THE INVENTION

Disclosed herein are methods for diagnosing cardiovascular disease. The methods comprise detection of citrullinated proteins and/or citrullinated peptides. Also disclosed herein are methods, compositions, and kits for diagnosing and/or treating cardiovascular disease.

BACKGROUND

Despite tremendous advances in cardiovascular research and clinical therapy, heart disease remains the leading cause of morbidity and mortality in western society and is growing in developing countries. Cardiovascular diseases (CVD) have been subjected to extensive study, covering all major pathological conditions: including ischemic heart disease (IHD) and heart failure (HF) the two primary causes of CVD. Heart failure is characterized by reduced blood supply to the heart muscle with resulting decreased function. It is also appreciated that treating heart failure patients with drugs (such as cardiac glycosides) augment pump function by increasing the contractility of cardiac myocytes and can improve hemodynamics and exercise tolerance. These observations led to the "hemodynamic hypothesis" that heart failure is primarily caused by defective cardiac myocyte contractility. It is important to point out that other factors— changes in cardiac structure (dilation), cell death (apoptosis), altered vascular structure and reactivity, abnormal energy utilization, and neurohormonal disturbances also contribute to the progression of CVD. Cardiac contractile function is, in part, regulated by post-translational modifications (PTMs) to the myofilament. This machinery is directly responsible for the force-generating process. Both dynamic and irreversible PTMs, like phosphorylation, occur to myofilament proteins and have been observed in numerous models of heart disease.

Importantly, IHD can occur acutely, resulting in myocardial stunning or myocardial infarction (heart attack) or chronically which is one common cause of heart failure. Interestingly, in the acute situation, intermittent ischemia events can be protective against a subsequently more severe ischemic event reducing cell death and injury to the heart. This is termed myocardial preconditioning and is known to occur to many other organs, including kidney and skeletal muscle. Preconditioning, in part reduces the drop in cellular pH and increase in calcium concentration that occurs with reperfusion. This condition can effect the peptidyl arginine deiminases (PADs) which are a family of calcium dependent enzymes that post-translationally convert arginine residues on substrate proteins to the non-standard amino acid citrulline.

The enzymatic conversion of arginine into citrulline occurs in physiological processes such as epidermal differentiation, formation of the hair follicle and differentiation of the myelin sheath during development of the central nervous system. It was first linked to human pathology by the demonstration of citrullinated proteins in the synovium of patients with rheumatoid arthritis. More recently, protein citrullination has been described in non-rheumatoid inflammatory synovitis and also in autoimmune neurodegenerative diseases such as multiple sclerosis and Alzheimer's disease. In light of these observations, we asked whether citrullination occurs in the heart and whether this modification will provide insights into the pathologies of specific disease states in cardiac. Furthermore, there have been no investigations to determine if PADs are present in the heart during health or disease events.

The incident rates of heart failure and diastolic dysfunction are increased in rheumatoid arthritis (RA) patients compared to non-RA controls, suggesting that myocardial remodeling occurs as part of the RA disease process. The phenotype of heart failure in RA differs from that of non-RA patients, characterized by fewer symptoms, lower blood pressure, and higher ejection fraction at presentation, suggesting that the pathophysiologic mechanisms underlying the progression to heart failure in RA patients may be different from those of the general population. Recently, it was reported that an association of higher concentration of serum anti-CCP antibodies with lower myocardial mass and smaller left ventricular chamber volume in RA patients without known cardiovascular disease; raising the possibility that RA-specific autoimmunity against citrullinated proteins might mediate changes to myocardial morphology that, in turn, may affect myocardial function. Citrullination, the post-translational modification of basic amino acid arginine to neutral amino acid citrulline results in basic charge loss which can influence the overall charge distribution, isoelectric point, as well as the ionic and hydrogen bond formation. This PTM is crucial as it can alter the physical and chemical properties of proteins, regulating protein folding, distribution, stability, activity and function. The reaction is catalyzed by a set of peptidyl arginine deiminase enzymes (PADs), that are abundant in the rheumatoid synovium but not restricted to RA.

In North America, infectious-cardiomyopathy can occur during or follow viral infections (e.g. coxsackievirus B3, adenoviruses or parvovirus B19). In fact, immunocardiomyopathy is an important cause of HF or sudden death especially in children and young adults. Therefore, we believe that myocardial citrullination would be more abundant in RA compared to other conditions, and that myocardial regions demonstrating citrullination would co-localize with evidence of tissue damage (i.e. myocarditis, fibrosis, etc.) and PADs.

SUMMARY

In an embodiment, the invention is directed to a method of diagnosing cardiovascular disease in a subject comprising detecting the presence of a citrullinated protein in a biological sample obtained from a subject. In another embodiment, modulation of peptidyl arginine deiminase activity is also contemplated.

In various embodiments, the present invention provides a method for treating, inhibiting, and/or reducing the severity of a cardiovascular disease in a subject, comprising: administering to the subject a therapeutically effective amount of one or more PAD inhibitors so as to treat, inhibit, and/or reduce the severity of the cardiovascular disease. In some embodiments, the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the method further comprises administering one or more additional therapies to the subject. In some embodiments, the additional therapies are selected from cholesterol-lowering agent, glucose-lowering agent, lipid-lowering agent, fat/adipose tissue mass-lowering agent, blood pressure lowering agent, dietary therapy, physical therapy, behavior therapy, surgery, drug therapy, or any combination thereof. In some embodiments, the PAD inhibitors are selected from F-amidine [N-α-benzoyl-N5-(2-fluoro-1-iminoethyl)-1-ornithine amide], 2-chloroacetamidine, Cl-amidine [N-α-benzoyl-N5-(2-chloro-1-iminoethyl)-1-ornithine amide], o-F-amidine [N-α-(2-carboxyl)benzoyl-N5-(2-fluoro-1-iminoethyl)-L-ornithine amide], o-Cl-amidine [N α-(2-carboxyl)benzoyl-N5-(2-Chloro-1-iminoethyl)-L-ornithine amide] and TDF tripeptide (Thr-Asp-F-amidine). In some embodiments, the therapeutically effective amount of the PAD inhibitor is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the PAD inhibitors are administered to the subject 1-3 times per day or 1-7 times per week. In some embodiments, the PAD inhibitors are administrated to the subject for 1-5 days, 1-5 weeks, 1-5 months, or 1-5 years. In some embodiments, the PAD inhibitors and the additional therapies are administered sequentially or simultaneously.

In various embodiments, the present invention provides a method for diagnosing and/or prognosis cardiovascular disease in a subject, comprising: obtaining a sample from the subject; detecting an amount of one or more citrullinated proteins in the sample from the subject; comparing the amount of the citrullinated proteins in the sample from the subject to an amount of one or more citrullinated proteins from a reference sample, wherein a change in the amount of the citrullinated proteins in the sample from the subject relative to the amount of the citrullinated proteins from the reference sample is indicative of cardiovascular disease in the subject; and administering and/or selecting and/or prescribing a treatment for the subject based on the diagnosis and/or prognosis. In some embodiments, the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the sample is selected from blood, plasma, serum and tissue. In some embodiments, the citrullinated protein is selected from the group consisting of myosin heavy chain, myosin binding protein C, tropomyosin al, tropomyosin α3, actin, titin, lipoprotein lipase, L-lactate dehydrogenase B chain, Alpha-1-antichymotrypsin, Caspase recruitment domain-containing protein 10, Zinc finger ZZ-type EF-hand domain-containing protein 1, and caskin 1. In some embodiments, the citrullinated protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO. 18. In some embodiments, the citrullinated protein is selected from the group consisting of myosin heavy chain, myosin binding protein C, tropomyosin α1, tropomyosin 3, actin, lipoprotein lipase, sulfhydryl oxidase 2, putative zinc finger protein 818, disintegrin and metalloproteinase domain-containing protein 10, titin, Zinc finger ZZ-type and EF-hand domain-containing protein 1, serpin, and tRNA-dihydrouridine synthase. In some embodiments, the citrullinated protein comprises an amino acid sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34. In some embodiments, the amount of the citrullinated protein is detected using mass spectrometry, high resolution mass spectrometry, tandem mass spectrometry, binding assay, immunoassay, antibody binding or immunohistochemistry. In some embodiments, the reference sample is obtained from a control subject, wherein the control subject does not have a cardiovascular disease. In some embodiments, the reference sample is obtained from the subject before the subject is treated for the cardiovascular disease. In some embodiments, the reference sample is from a subject that has been successfully treated for the cardiovascular disease.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 1A) The ureido group of citrulline is modified by 2,3-butanedione and antipyrine to form a modified citrulline residue. The mass is increased by 239 Da. FIG. 1B) MS/MS spectrum illustrating the identification of the derivatized citrullines.

Site specific endogenous citrullination of control versus HF samples (IHD, IDCM). Myosin heavy chain has four citrullinated sites; tropomyosin also has four citrullinated sites; however, there is a difference between the site specificity of modified residues.

Figure 3A:
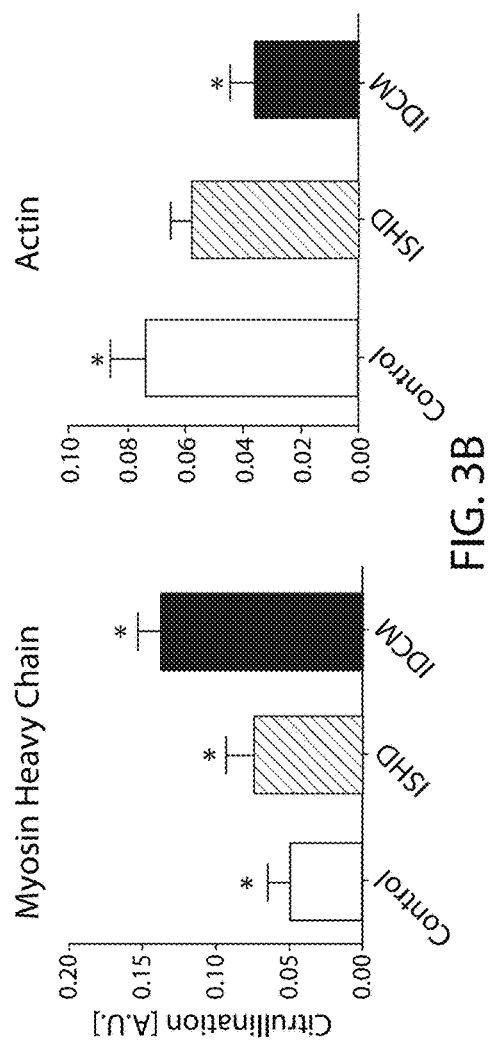
Figure 3B:
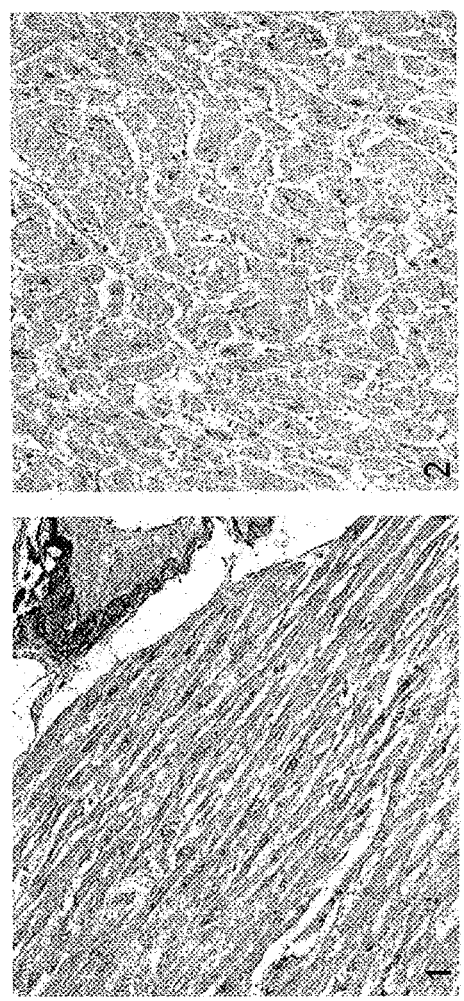

FIG. 3A-FIG. 3B: FIG. 3A) Detection of citrullinated proteins in heart homogenate obtained from control and HF patients (IHD, IDCM). Citrullination of myofilament proteins was expressed relative to direct blue staining to correct for differences in protein loading. *p<0.05 donor vs. IHD vs. IDCM in t-test. IN IDCM tissue, a significant increase was seen in myosin heavy chain citrullination vs. control and IHD. A small decrease of actin citrullination was observed in donor tissue vs. IDCM samples. FIG. 3B) Immunohistochemical staining of citrullinated proteins in heart from control patients. (1) Citrullinated proteins were detected in the myrofibrils of control. (2) In the negative control the myofibrils are clearly unstained.

FIG. 4A-FIG. 4B: Verification of the high abundant proteins was carried out with 2D-DIGE analysis of control and PAD2 treated human heart (left ventricle). Samples were labeled with Cy2 (internal control), Cy3 (untreated) and Cy5 (treated). Each gel contains 150 µg of total protein separated by pI ranges 4-7 in the first dimension and 10% linear polyacrylamide gel in the 2D. FIG. 4A) Representative large 2D-DIGE gel of cytoplasmic and FIG. 4B myofilament enrich fraction with green shift indicating citrullination. Relevant images were captured by excitation with different laser using Typhoon 9210. The arrows indicate differentially regulated protein spots determined by image analysis and identified by LC-MS/MS. Proteins are numbered according to Table 2.

FIG. 5A-FIG. 5D: RT-PCR analysis of expression level of PAD isoforms in heart from control mouse (FIG. 5A, FIG. 5B) mouse keratinocytes (FIG. 5C), loading standard actin (FIG. 5D). The PCR products PAD2 is seen in all types of samples; PAD 4 and PAD1 is seen in cardiac fibroblast and keratinocytes. PAD3 has not been seen in any of the samples.

Figure 6:
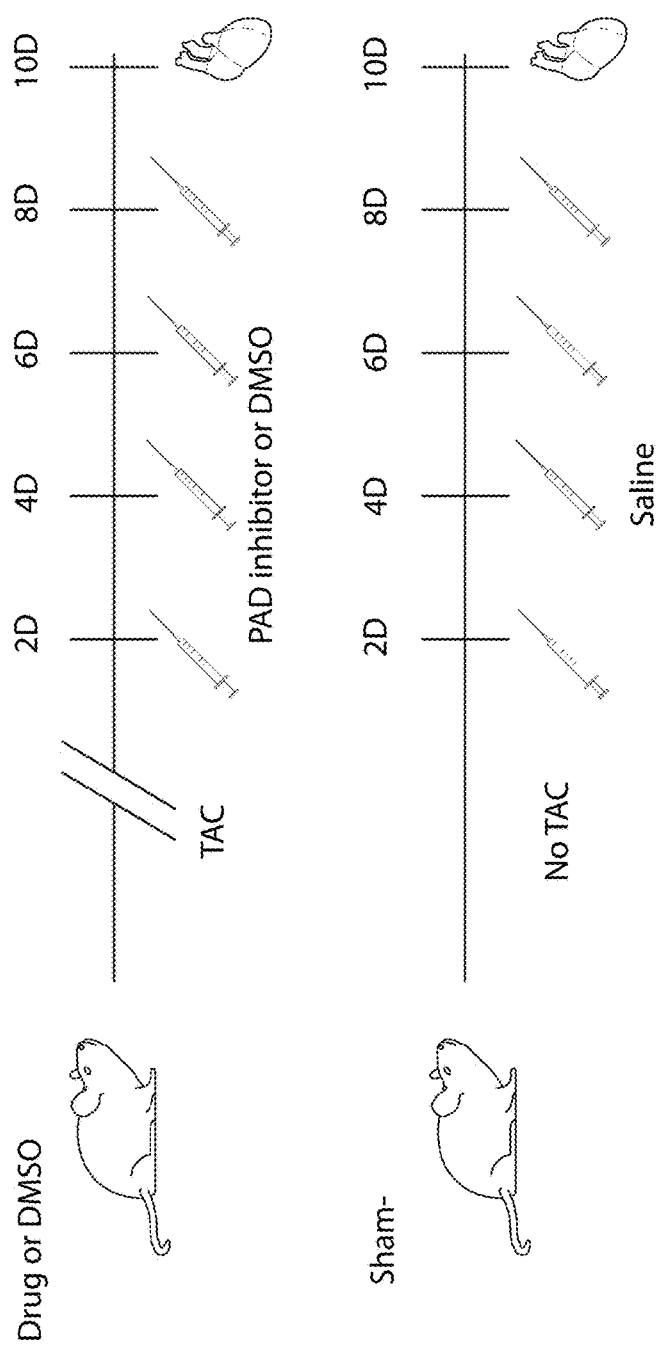

FIG. 6: Overview of the experimental workflow used to investigate the role of PAD inhibition in heart citrullinated proteome using mouse models of heart failure induced by pressure overload. Injection Protocol: PAD inhibitor: 20 mg/kg IP; PAD stock: PAD 100 ug/ul dissolve in DMSO; Injection Volume 1 Set: 300 ul of saline plus stock; Injection Volume 2 Set: 150 ul of saline plus stock; Daily injection or every second day; DMSO control: The amount as in the drug plus saline.

FIG. 7A: Cardiac dysfunction (heart weight/post body weight) in response to TAC from the various experimental groups.

Figure 7B:
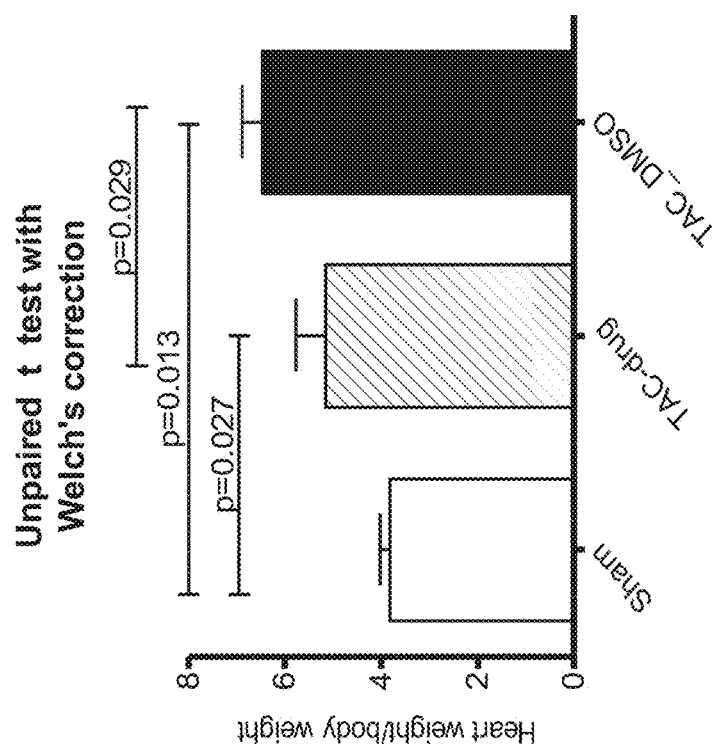

FIG. 7B: Average weights of hearts from all mice described in FIG. 7A (only values in parenthesis are plotted). n=4 for each drug treated group; n=3 for TAC untreated group; n=3 for Sham group.

FIG. 7C: Higher-magnification views of hematoxylin/eosin stains of transverse sections of the same hearts as in FIG. 7A. Darker area are normal, lighter stained area are fibrotic tissue. (Magnifications: ×20.).

FIG. 8A: Immunoblot analysis of Smad4 protein expression in the hearts of either untreated (Sham) mice or mice after 10 days of TAC-induced pressure overload (n=6 mice per group) drug treated (TAC drug) and failing human hearts (TAC DMSO) (n=3 independent samples per group). *P<0.05 versus Con; Student's t-test.

FIG. 8B: Immunoblot analysis of Smad2/pERK proteins expression in indicated experiments (n=6 for each drug treated group; n=3 for TAC untreated group; n=3 for Sham group). *P<0.05 versus Con; Student's t-test.

FIG. 8C: Characterization of fibrosis-handling protein by immunoblot analysis of vimentin in heart lysates of Sham and TAC drug and TAC untreated mice.

FIG. 8D: Induction of TGF-β 1 and activation of TGF-β signaling pathways in the pressure overloaded mouse heart. Because TGF-β plays a crucial role in the transition from inflammation to fibrosis we examined the TGF-β1 protein expression in the TAC hearts treated with PAD inhibitor. Fibrotic remodeling of the ventricle was associated with marked upregulation of TGF-β1 after 10 days of TAC and with activation of TGF-β signaling evidenced by markedly increased levels of Smad 4 and Smad2 (FIG. 8A and FIG. 8B).

FIG. 8E: PAD2 induction in the pressure-overloaded heart. Immunoblot analysis of PAD2 isoform in the hearts of either untreated (Sham) mice or mice after 10 days of TAC-induced pressure overload (n=6 mice per group) drug treated (TAC drug) and failing human hearts (TAC DMSO) (n=3 independent samples per group). *P<0.05 versus Con; Student's t-test.

FIG. 9: Table 4. Summary of the seven proteins. DIGE and mass spectrometry: DIGE images of the nine gels enabled localization of variation spots. Spots detected by CyDyes staining were excised and subjected for identification. In total, up to 25 different spots were detected on the nine gels. Orbi trap LTQ was used to analyze the peptides after in-gel digestion of each spot. A total of 25 protein spots, only 7 were successfully identified. Table 4 shows the proteins which were identified.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

Definitions

The following terms are used as defined below throughout this application, unless otherwise indicated.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

"Marker" or "biomarker" are used interchangeably herein, and in the context of the present invention refer to a protein or peptide that has specific citrullinated amino acid residues or the enzyme itself, PAD 1, PAD2 or PAD4 (of a particular specific identity or apparent molecular weight) which is differentially present in a sample taken from patients having a specific disease or disorder as compared to a control value, the control value consisting of, for example, average or mean values in comparable samples taken from control subjects (e.g., a person with a negative diagnosis, normal or healthy subject). Biomarkers may be determined as specific peptides or proteins (Table 1A or Table 1B) which may be detected by antibodies or mass spectroscopy. In some applications, for example, a mass spectroscopy or other profile or multiple antibodies may be used to determine multiple biomarkers, and differences between individual biomarkers and/or the partial or complete profile may be used for diagnosis. This can include detection of the enzyme or a protein it has citrullinated, alone or in combination.

The phrase "differentially present" refers to differences in the quantity and/or the frequency of a marker present in a sample taken from patients having a specific disease or disorder as compared to a control subject. For example, a marker can be present at an elevated level or at a decreased level in samples of patients with the disease or disorder compared to a control value (e.g. determined from samples of control subjects). Alternatively, a marker can be detected at a higher frequency or at a lower frequency in samples of patients compared to samples of control subjects. A marker can be differentially present in terms of quantity, frequency or both as well as a ratio of differences between two or more specific modified amino acid residues and/or the enzyme itself.

A marker, compound, composition or substance is differentially present in a sample if the amount of the marker, compound, composition or substance in the sample is statistically significantly different from the amount of the marker, compound, composition or substance in another sample, or from a control value. For example, a compound is differentially present if it is present at least about 120%, at least about 130%, at least about 150%, at least about 180%, at least about 200%, at least about 300%, at least about 500%, at least about 700%, at least about 900%, or at least about 1000% greater or less than it is present in the other sample (e.g. control), or if it is detectable in one sample and not detectable in the other.

Alternatively, or additionally, a marker, compound, composition or substance is differentially present between samples if the frequency of detecting the marker, etc. in samples of patients suffering from a particular disease or disorder, is statistically significantly higher or lower than in the control samples or control values obtained from healthy individuals. For example, a biomarker is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples. These exemplary values notwithstanding, it is expected that a skilled practitioner can determine cut-off points, etc. that represent a statistically significant difference to determine whether the marker is differentially present.

The term "diagnosis," or "dx," refers to the identification of the nature and cause of a certain phenomenon. As used herein, a diagnosis typically refers to a medical diagnosis, which is the process of determining which disease or condition (e.g., a cardiovascular disease) explains a symptoms and signs. A diagnostic procedure, often a diagnostic test or assay, can be used to provide a diagnosis. A diagnosis can comprise detecting the presence of a disease or disorder (e.g., a cardiovascular disease) or the risk of getting a disease or disorder.

The term "prognosis," or "px," as used herein refers to predicting the likely outcome of a current standing. For example, a prognosis can include the expected duration and course of a disease or disorder (e.g. a cardiovascular disease), such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Diagnostic" means identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g. when positive assay results are obtained). In the latter context, "detecting" and "diagnosing" are considered synonymous.

By "at risk of" is intended to mean at increased risk of, compared to a normal subject, or compared to a control group, e.g. a patient population. Thus a subject carrying a particular marker may have an increased risk for a specific disease or disorder, and be identified as needing further testing. "Increased risk" or "elevated risk" mean any statistically significant increase in the probability, e.g., that the subject has the disorder. In some embodiments the risk is increased by at least 10%. In some embodiments, the risk is increased by at least 20%. In some embodiments the risk is increased by at least 50% over the control group with which the comparison is being made.

A "test amount" of a marker refers to an amount of a marker present in a sample being tested. A test amount can be either in absolute amount (e.g., g/ml) or a relative amount (e.g., relative intensity of signals).

A "diagnostic amount" of a marker refers to an amount of a marker in a subject's sample that is consistent with a diagnosis of a particular disease or disorder. A diagnostic amount can be either in absolute amount (e.g., g/ml) or a relative amount (e.g., relative intensity of signals).

A "control amount" of a marker can be any amount or a range of amount which is to be compared against a test amount of a marker. For example, a control amount of a marker can be the amount of a marker in a person who does not suffer from the disease or disorder sought to be diagnosed. A control amount can be either in absolute amount (e.g., µg/ml) or a relative amount (e.g., relative intensity of signals).

The terms "polypeptide," "peptide" and "protein" are used interchangeably herein to refer to a polymer of α-amino acid residues, in particular, of naturally-occurring α-amino acids. The terms apply to amino acid polymers in which one or more amino acid residue is an analog or mimetic of a corresponding naturally-occurring amino acid, as well as to naturally-occurring amino acid polymers. Polypeptides can be modified, e.g., by the addition of carbohydrate residues to form glycoproteins, phosphorylation to form phosphoproteins, and a large number of chemical modifications (oxidation, deamidation, amidation, methylation, formylation, hydroxymethylation, guanidination, for example) as well as degraded, reduced, or cross-linked. The terms "polypeptide," "peptide" and "protein" include all unmodified and modified forms of the protein. A peptide would have a citrullinated residue or is part of the PAD enzyme.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct analysis by mass spectrometry of intact protein or peptides (one or more peptide can be assessed) that has a potential citrullinated residue or part of the PAD enzyme. Citrullinated Arg as part of a protein or peptide can be detected directly by MS or via chemical derivatization.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution. Further, chemical binding to the citrullinated residue can occur directly.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

"Methods for detecting citrullination" refer to the mass spectrometry (MS) base methods used to detect citrullinated peptides, polypeptides and proteins. The methods include but are not restricted to neutral loss of 1 Da when deimination occurs on Arg; neutral loss of isocyanic acid from unmodified citrulline and used this ion as a diagnostic marker for detecting protein citrullination; derivatization when chemical modification of 238 Da or 239 Da occurs on Cit residue (can be monitored at the peptide and protein level); enrichment of citrullinated peptides (or proteins) that is based on the specific reaction of glyoxal derivatives that is immobilized on beads/column/matrix reacts exclusively with the ureido group of the citrulline residue at low pH. As well, MS using a targeted method like multiple or selective reaction monitoring can be used to quantify the modified peptide directly. As used herein, a labeled (e.g. N15 or chemical with additional stable isotope) peptide of known concentration is added to the sample and compared directly to the endogenous (unlabeled) corresponding peptide.

The terms "subject", "patient" or "individual" generally refer to a human, although the methods of the invention are not limited to humans, and should be useful in other animals (e.g. birds, reptiles, amphibians, mammals), particularly in mammals, since albumin is homologous among species. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In various embodiments, the subject is mouse or mice. In various embodiments, the subject is human.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "threshold" as used herein refers to the magnitude or intensity that must be exceeded for a certain reaction, phenomenon, result, or condition to occur or be considered relevant. The relevance can depend on context, e.g., it may refer to a positive, reactive or statistically significant relevance.

The term "condition" (physiological state or biological state or health state) is understood in the present invention as status of a subject that can be described by physical, mental or social criteria. It includes as well so-called "healthy" and "diseased" conditions, therefore it is not limited to the WHO definition of health as "a state of complete physical, mental, and social well-being and not merely the absence of disease or infirmity." but includes disease and infirmity.

The term "disease" refers to an abnormal condition affecting the body of an organism. The term "disorder" refers to a functional abnormality or disturbance. The terms disease or disorder are used interchangeably herein unless otherwise noted or clear given the context in which the term is used. In some embodiments the disease is a cardiovascular disease.

A "cardiovascular disease," as used herein, refers to a disorder of the heart and blood vessels, and includes disorders of the arteries, veins, arterioles, venules, and capillaries. Non-limiting examples of cardiovascular diseases include congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease.

In some embodiments the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof. In some embodiments, the cardiovascular disease is selected from ischemic heart disease, cardiomyopathy, hypertensive heart disease, and heart failure, or any combination thereof.

As used herein, the term "heart failure" refers to the pathophysiological state in which the heart is unable to pump blood at a rate commensurate with the requirements of the metabolizing tissues or can do so only from an elevated filling pressure.

The term "state of health" includes at least one condition as defined herein. It may also include a plurality of different conditions. In some embodiments, the state of health is a healthy state. In some embodiments, the state of health is a diseased state.

The term "physiological state" refers to a state determined through physiological measurement, which depicts a subject's mental resources or physical resources or combination thereof. Non-limiting examples of physiological measurements include the measurement of heart rate, blood pressure, stroke volume, and cardiac output as indices of overall cardiovascular performance and health.

The term "healthy state" or "normal state" means that the state of a subject (e.g., physiological state or biological state or health state, etc.) is not abnormal or does not comprise a disease or disorder.

A "healthy subject" or "normal subject" is a subject that does not have a disease or disorder.

The term "preventative treatment" means maintaining or improving a healthy state or non-diseased state of a healthy subject or subject that does not have a disease. The term "preventative treatment" also means to prevent or to slow the appearance of symptoms associated with a condition, disease, or disorder. The term "preventative treatment" also means to prevent or slow a subject from obtaining a condition, disease, or disorder.

The term "phenotype" as used herein comprises the composite of an organism's observable characteristics or traits, such as its morphology, development, biochemical or physiological properties, phenology, behavior, and products of behavior.

"Sample" is used herein in its broadest sense. A sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Subject samples usually comprise derivatives of blood products, including blood, plasma and serum. In some embodiments the sample is a biological sample. The term "biological sample" as used herein denotes a sample taken or isolated from a biological organism. Non-limiting examples of samples or biological samples include cheek swab; mucus; whole blood, blood, serum; plasma; urine; saliva; semen; lymph; fecal extract; sputum; other body fluid or biofluid; cell sample; and tissue sample (e.g. heart biopsy) etc. The term also includes a mixture of the above-mentioned samples or biological samples. The term "sample" also includes untreated or pretreated (or pre-processed) biological samples. In some embodiments, a sample or biological sample can comprise one or more cells from the subject. In some embodiments subject samples or biological samples comprise derivatives of blood products, including blood, plasma and serum. In some embodiments the sample is blood, plasma, serum, or tissue. In some embodiments, the sample or biological sample is whole blood, blood, serum, plasma, and tissue sample (e.g. heart biopsy).

The terms "body fluid" or "bodily fluids" are liquids originating from inside the bodies of organisms. Bodily fluids include amniotic fluid, aqueous humour, vitreous humour, bile, blood (e.g., serum), breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. "Biological sample" also includes a mixture of the above-mentioned body fluids. "Biological samples" may be untreated or pretreated (or pre-processed) biological samples.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaXis blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device; a tissue sample collection device.

The term "modulation of specific PAD isoforms" include, but are not limited to, increasing or decreasing the activity of endogenous PAD isoforms using gene therapy, siRNA, known inhibitors of PADs, or site-directed mutagenesis.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom, condition, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition, disease, or disorder as well as those prone to have the condition, disease, or disorder, or those in whom the condition, disease, or disorder is to be prevented. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "preventative treatment" means maintaining or improving a healthy state or non-diseased state of a healthy subject or subject that does not have a disease. The term "preventative treatment" also means to prevent or to slow the appearance of symptoms associated with a condition, disease, or disorder. The term "preventative treatment" also means to prevent or slow a subject from obtaining a condition, disease, or disorder.

The phrase "therapeutically effective amount" as used herein means that amount of an agent, compound, material, or composition comprising the same which is effective for producing some desired therapeutic effect in at least a sub-population of cells in an animal at a reasonable benefit/risk ratio applicable to a medical treatment. Determination of a therapeutically effective amount is well within the capability of those skilled in the art. Generally, a therapeutically effective amount can vary with the subject's history, age, condition, as well as the severity and type of the medical condition in the subject, and administration of other pharmaceutically active agents. In some embodiments, the compound is one or more PAD inhibitors.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a cardiovascular disease, delay or slowing of a cardiovascular disease, and amelioration or palliation of symptoms associated with a cardiovascular disease.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

Post-translational modification (PMT) of arginine to citrulline by peptidylarginine deiminases (PADs) is abundant in rheumatoid synovium, and autoimmunity against citrullinated proteins is highly specific for RA (Giles et al. *Arthritis Rheum* 2010; 62:940-951) and a strong predictor of articular damage (van Gaalen et al. *Arthritis Rheum* 2004; 50(7):2113-2121). Citrullination is observed in tissues other than rheumatoid synovium, and typically in conditions characterized by inflammation/autoimmunity, such as multiple sclerosis, inflammatory bowel disease, and polymyositis (Makrygiannakis et al. *Ann Rheum Dis* 2006; 9:1219-1222) ischemic heart disease (IHD) and heart failure (HF). While it is unclear whether immune targeting of citrullinated proteins mediates any of the phenotypic features of these disorders, the abundant citrullination observed in these varied disorders suggests that other tissues, such as the myocardium, may also demonstrate post-translational citrullination.

Protein citrullination is catalyzed by a family of $Ca^{2+}$ dependent enzymes, peptidyl arginine deiminases (PADs), which deiminate positively charged arginine residues to neutral citrulline which can change the structure and function of a protein due to the loss of the basic character. This post-translational modification (PTM) has become an area of interest due to its role in several physiological and pathological processes. Physiological processes include epithelial terminal differentiation, gene expression regulation, and apoptosis. Multiple sclerosis, Alzheimer's disease and Rheumatoid arthritis (RA) are examples of human diseases where protein citrullination involvement has been demonstrated. We propose that protein citrullination plays a role in the progression and development of ischemia/reperfusion injury or heart failure (HF) alone or in terms of RA and other diseases. Additionally, some of the protein targets that undergo citrullination in rheumatoid synovium (i.e. vimentin, enolase, fibronectin) and are targets for anti-CCP antibodies in RA are also present in the myocardium (Giles et al., *Arthritis Rheum* 2010, 62:940-951). We show that proteins in the myocardium serve as substrates for citrullination. Furthermore, and not to be limited to a particular mechanism of dysfunction, it is possible that citrullination of the fundamental contractile element in the myofilament could contribute to myocardial dysfunction. We show that protein citrullination occurs in normal hearts (healthy) and that the protein citrullination status changes with heart disease. We have identified citrullinated proteins and their modified amino acid residues in tissue isolated from the heart as well as from cardiac myocytes. The number of modified proteins and the modified amino acids can reflect different heart disease phenotypes. In one embodiment, the invention focuses on the detection of the citrullinated proteins and sites of citrullination of the intact or degraded protein in plasma or serum as well as tissue (e.g. biopsy). In another embodiment, the citrullinated proteins can be used as a diagnostic marker for myocardial disease. In another embodiment, PAD activity may be modulated.

Regulation and augmentation of myocardial contractility is required in many disease settings. Citrullination of key cardiac specific myofilament proteins occur and thus, could have a pivotal role in regulating the contractile activity of the heart. Regulation (increase or decrease) of citrullination could allow control of heart function in acute (such as in ischemia reperfusion injury) and chronic (such as failing heart) disease phenotypes. Detection of citrullinated proteins in tissue or body fluids (e.g., blood, plasma and serum) can be a biomarker(s) for diagnosis, prognosis or risk stratification in patients with cardiac disease including myocardial injury and heart failure. The citrullinated cardiac proteins may act as immune targets for circulating autoantibodies, especially if secreted or released following myocardial injury.

Role of cardiomyopathy in RA: Increased evidence of cardiovascular morbidity and mortality in RA patients has been only recently recognized. Studies have shown that the risk of myocardial infarction (MI), heart failure (HF) and stroke is higher in patients with RA and can cause up to 40% of deaths in these patients (Wolfe et al., *Arthritis Rheum* 2008, 9:2612-2621; Levy et al., *Clin Exp Rheumatol* 2008, 4:673-679; Nadareishvili et al., *Arthritis Rheum* 2008, 8:1090-1096; Lopex-Longo et al., *Arthritis Rheum* 2009 4:419-424; Sihvonen et al. *Scand J Rheumatol* 2004 33:221-227). It is speculated in rheumatoid arthritis that the underlying inflammatory processes of the disease contributes to production/induction of anti-CCP antibodies, which precedes the onset of RA, and can be independently associated with the development of ischemic heart disease (Turesson et al., *Ann Rheum Dis* 2007, 66:70-75). Anti-CCP antibodies are specific markers for RA (Yamada et al., *Future Rheumatology* 2006, 2:249-258). Citrullination also occurs in autoimmune neurodegenerative diseases such as multiple sclerosis and Alzheimer's disease (Nicholas et al., *J Comp Neurol* 2003, 2:51-66; Shida-Yamamoto et al., *Journal of Investigative Dermatology* 2002, 118:282-287) as well as in various general biological processes such as epithelial terminal differentiation, gene expression regulation, and apoptosis (Shibata et al., *Journal of Dermatological Science* 2009, 53:34-39; Mastronardi et al., *J Neurosci* 2006, 44:11387-11396; Lundberg et al., *Arthritis Rheum* 2008, 58:3009-3019; Raptopoulou et al., *Crit Rev Clin Lab Sci* 2007, 44:339-363; Gabriel et al., *Arthritis Rheum* 1999, 42:415-420). We investigated fractions of human heart and determined the citrullinated protein in healthy vs. HF individuals. Furthermore, we determined whether the proteins that have modification(s) change with disease or if modification can have an influence on protein function.

Figure 1A:
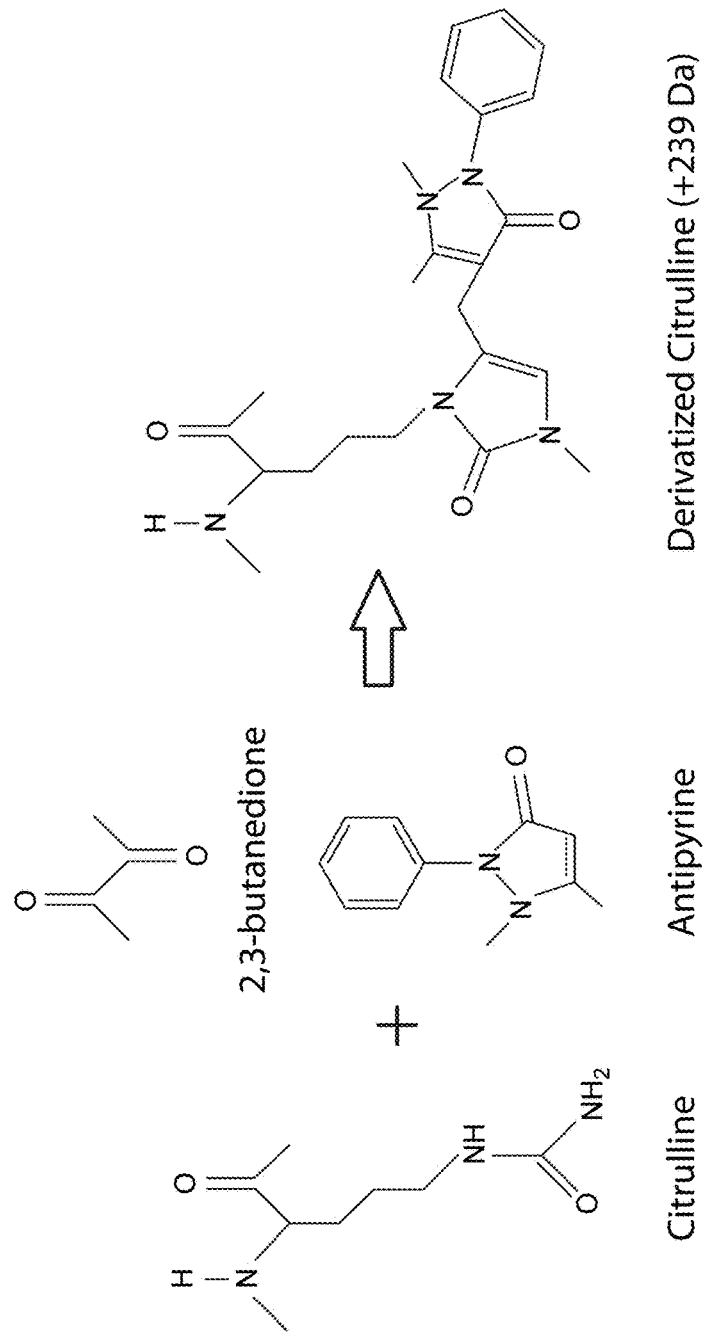
FIG. 1A-FIG. 1B: Citrullination derivation scheme and its detection by mass spectroscopy.
Figure 1B:
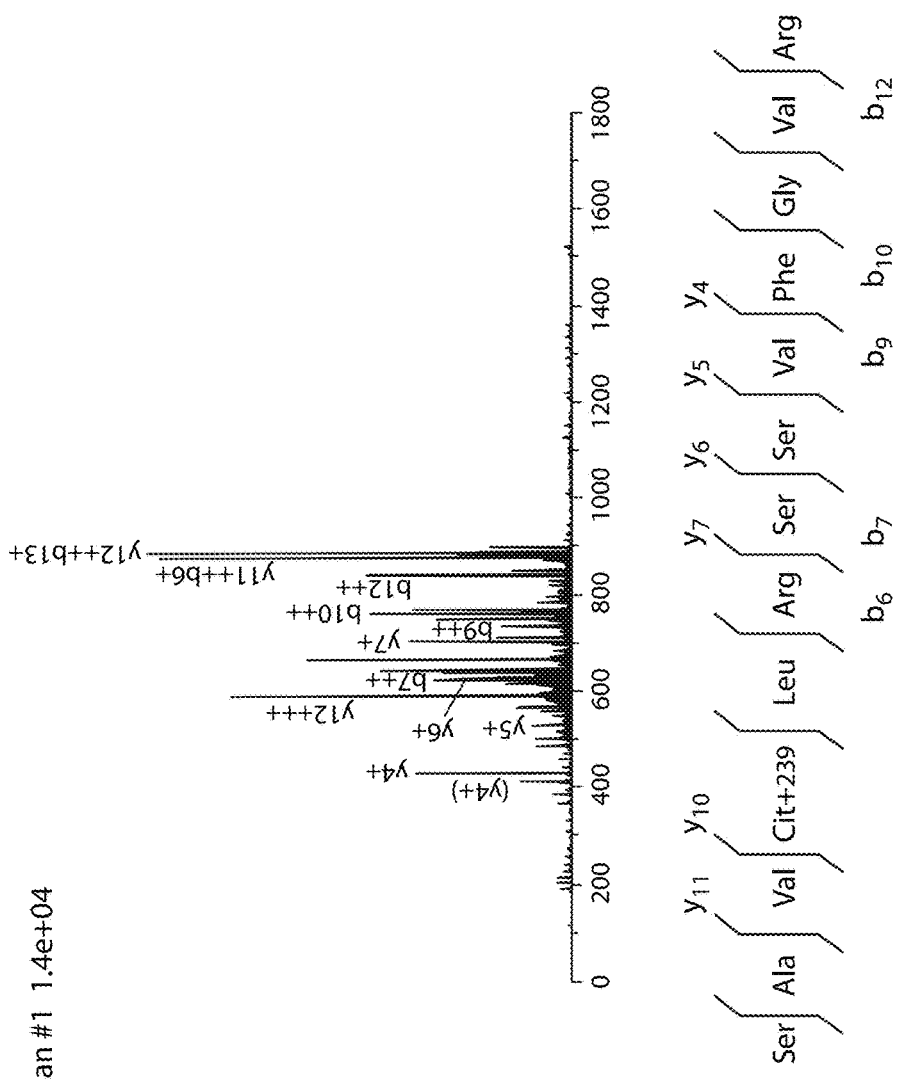

Citrullination (also known as deimination) is a PTM (posttranslational modification) characterized by the conversion of a positively charged amino acid residue, arginine, to a neutrally charged citrulline (FIG. 1A-FIG. 1B). Introduction of citrulline can dramatically change the structure and function of a protein due to the loss of the strong basic character (pI=10.76) which influences the overall charge distribution, isoelectric point, and the ionic and hydrogen bond forming abilities of the protein. While not wishing to be limited to theory, such changes may alter the protein structure and results in a somewhat looser, more open configuration (Tarcsa et al., *J Biol Chem* 1996, 48:30709-30716). Therefore, citrullination may also influence the interaction of the molecule with other proteins. For example, citrullination of vimentin filaments can induce almost complete depolymerization, disrupting the cell's cytoskeletal network (Inagaki et al., *J Biol Chem* 1989, 264:18119-18127; Backs et al., *Circulation Research* 2006, 98:15-24). In histones, citrullination was recently found to have a repressive effect in nucleosome-nucleosome interactions, which consequently affects higher-order chromatin structure (Spencer et al., *Gene* 1999, 240:1-12). Recent work has demonstrated the importance of chromatin remodeling in the control of cardiac growth and gene expression in response to acute and chronic stress stimuli. Additionally, arginine methylation in histones also affects chromatin structure. Importantly for our study, it has been shown that the enzymes utilized in citrullination can indirectly antagonize arginine methylation (Spencer et al., *Gene* 1999, 240:1-12). This functional connection between citrullination and deacetylation of histones may have some undercover implication in remodeling or gene expression in response to acute and chronic stress stimuli leading to altered cardiac function.

Herein, the inventors disclose citrullinated proteins in healthy patients (Table 1A) and in heart failure (diseased) patients (Table 1B). Citrullination occurs in specific proteins, including the myofilament proteins; tropomyosin, myosin (heavy and light chain) and myosin binding protein C, suggesting that this modification could also be seen in skeletal muscle, which is also predominated by these myofilament proteins. With this information, it is now possible to diagnose susceptibility to cardiovascular disease and susceptibility to autoimmunity to citrullinated proteins. Accordingly, methods of diagnosing cardiovascular disease are disclosed. Methods of diagnosing susceptibility to autoimmunity to citrullinated proteins in cardiovascular disease are disclosed. Either method includes the detection of citrullinated proteins in tissue or body fluids, including blood, plasma or serum.

TABLE 1A

List of citrullinated protein in healthy individuals identified by the targeted analysis using MS/MS (tandem mass spectrometry)

| Protein ID | Modified residue in sequence | Protein Function |
| --- | --- | --- |
| Myosin heavy chain | $Arg_{1479}$SerLeuSerThrGluLeuPheLys (SEQ ID NO: 1) $Arg_{1176}$AspLeuGluGluAlaThrLeuGlnHisGlu AlaThrAlaAlaAlaLeuArgLys (SEQ ID NO: 2) HisArgLeuGlnAsnGluIleGluAspLeuMetVal AspValGluArg$_{1434}$Ser (SEQ ID NO: 3) LysLysLeuAlaGlnArg$_{1400}$LeuGlnGluAlaGlu GluHisValGlu (SEQ ID NO: 4) | Muscle contraction. |
| Myosin binding protein C, cardiac | $Arg_{696}$ProAlaProAspAlaProGluAspThrGly AspSerAspGluTrpValPheAspLys (SEQ ID NO: 5) | Muscle contraction and hold the thick filament together. |
| Tropomyosin α 1 | GluAspArg$_{220}$TyrGluGluGluIleLys (SEQ ID NO: 6) GluThrArg$_{238}$AlaGluPheAlaGluArgSerVal ThrLysLeuGluLys (SEQ ID NO: 7) | Plays a central role in the calcium dependent regulation of muscle contraction |
| Tropomyosin α 3 | AlaGluGluAlaAspArg$_{124}$LysTyrGluGluVal AlaArgLys (SEQ ID NO: 8) | Plays a role, in association with the troponin complex, in regulation of vertebrate striated muscle contraction |
| Actin | AlaGlyPheAlaGlyAspAspAlaProArgAlaVal PheProSerIleValGlyArgProArg$_{39}$HisGln (SEQ ID NO: 9) | Stretch and contractility activity. |
| Titin | ValAsnSerArg$_{15172}$ProIleLysAspLeuLys (SEQ ID NO: 10) TyrArg$_{31811}$IleGlnGluPheLysGlyGlyTyrHis (SEQ ID NO: 11) AspIleLeuIleProProGluGlyGluLeuAspAla AspLeuArg$_{20535}$Lys (SEQ ID NO: 12) | Key component in the assembly and functioning of vertebrate striated muscles; it contributes to the fine balance of forces between the two halves of the sarcomere. |
| Lipoprotein lipase | ValIleAlaGluArg$_{254}$GlyLeuGlyAspValAsp GlnLeuValLys (SEQ ID NO: 13) | Hydrolysis of triglycerides of circulating chylomicrons and very low density lipoproteins (VLDL). Binding to heparin sulfate proteoglycans at the cell surface is vital to the function. |
| L-lactate dehydrogenase B chain | IleValValValThrAlaGlyValArg$_{100}$GlnGln GluGlyGluSerArgLeuAsnLeuVal (SEQ ID NO: 14) | Catalytic activity (S)-lactate + $NAD^+$ = pyruvate + NADH. |

TABLE 1A-continued

List of citrullinated protein in healthy individuals identified by the targeted analysis using MS/MS (tandem mass spectrometry)

| Protein ID | Modified residue in sequence | Protein Function |
| --- | --- | --- |
| Alpha-1 antichymotrypsin | $Arg_{184}$LeuTyrGlySerGluAlaPheAlaThrAsp PheGlnAspSerAlaAlaAlaLysLysLeuIle (SEQ ID NO: 15) | Can inhibit neutrophil cathepsin G and mast cell chymase, both of which can convert angiotensin-1 to the active angiotensin-2. |
| Caspase recruitment domain-containing protein 10 | Ser$Arg_{228}$AspLeuGlnLeuAlaValAspGlnLeu LysLeuLys (SEQ ID NO: 16) | Activates NF-kappa-B via BCL10 and IKK. |
| Zinc finger ZZ-type and EF-hand domain-containing protein 1 | LysLeuAspProLeuGluGlyLeuAspGluProThr $Arg_{2464}$ (SEQ ID NO: 17) | Protein binding |
| Caskin 1 | $Arg_{1305}$GlnProProAlaAlaLeuAlaLysProPro GlyThrProProSerLeuGlyAlaSerProAlaLys (SEQ ID NO: 18) | May link the scaffolding protein CASK to downstream intracellular effectors |

TABLE 1B

List of citrullinated proteins found in HF patients by the targeted analysis using MS/MS

| Protein ID | Modified residue in sequence | Protein Function |
| --- | --- | --- |
| Myosin heavy chain | $Arg_{1479}$SerLeuSerThrGluLeuPheLys (SEQ ID NO: 19) LeuIleSerGlnLeuThr$Arg_{1303}$GlyLys LeuThrTyrThrGlnGlnLeuGluAspLeu Lys (SEQ ID NO: 20) Gln$Arg_{1397}$LeuGlnAspSerGluGluGln ValGluAlaValAsnAlaLys (SEQ ID NO: 21) | Muscle contraction. |
| Myosin binding protein C, cardiac | $Arg_{896}$ProAlaProAspAlaProGluAsp ThrGlyAspSerAspGluTrpValPheAsp Lys (SEQ ID NO: 22) GluThr$Arg_{238}$AlaGluPheAlaGluArg SerValThrLysLeuGluLys (SEQ ID NO: 23) | Muscle contraction and hold the thick filament together. Plays a central role in the calcium dependent regulation of muscle contraction |
| Tropomyosin 3 | LeuGluGluAlaGluLysAlaAlaAspGlu SerGluArgGlyMetLysValIleGluAsn $Arg_{134}$AlaLeuLys (SEQ ID NO: 24) | Binds to actin filaments, regulates of vertebrate striated muscle contraction |
| Actin | AlaGlyPheAlaGlyAspAspAlaProArg AlaValPheProSerIleValGlyArgPro $Arg_{39}$HisGln (SEQ ID NO: 25) | Stretch and contractility activity. |
| Lipoprotein lipase | ValIleAlaGlu$Arg_{254}$GlyLeuGlyAsp ValAspGlnLeuValLys (SEQ ID NO: 26) | Hydrolysis of triglycerides of circulating chylomicrons and very low density lipoproteins (VLDL). Binding to heparin sulfate proteoglycans at the cell surface is vital to the function. |
| Sulfhydryl oxidase 2 | LeuPheProGly$Arg_{367}$ProProValLys (SEQ ID NO: 27) | Catalyzes the oxidation of sulhydryl groups to disulfides with the reduction of oxygen to hydrogen peroxide. |
| Putative zinc finger protein 818 | AsnAspGlu$Arg_{224}$AsnTyrArgGluIle ProAlaIleLysIleLys (SEQ ID NO: 28) | May be involved in transcriptional regulation. |
| Disintegrin and metalloproteinase domain-containing protein 10 | LeuAla$Arg_{656}$LeuLysLys (SEQ ID NO: 29) | Responsible for the proteolytic release of TNF-alpha and other cell-surface proteins, including heparin-binding epidermal growth-like factor, ephrin-A2 |

TABLE 1B-continued

List of citrullinated proteins found in HF patients by the targeted analysis using MS/MS

| Protein ID | Modified residue in sequence | Protein Function |
| --- | --- | --- |
| Titin | TyrArg$_{31811}$IleGlnGluPheLysGlyGly TyrHis (SEQ ID NO: 30) LeuSerGlyValLeuThrValLysAlaGly AspThrIleArg$_{19055}$ (SEQ ID NO: 31) | Key component in the assembly and functioning of vertebrate striated muscles; it contributes to the fine balance of forces between the two halves of the sarcomere. |
| Zinc finger ZZ-type and EF-hand domain-containing protein 1 | LysLeuAspProLeuGluGlyLeuAspGlu ProThrArg$_{2454}$ (SEQ ID NO: 32) | Protein binding |
| Serpin | PheTyrGlnThrSerValGluSerThrAsp PheAlaAsnAlaProGluGluSerArg$_{144}$ LysLys (SEQ ID NO: 33) | Act as a protease inhibitor to modulate the host immune response against tumor cells. |
| tRNA-dihydro-uridine synthase | GlyGlnGluLysThrCysArg$_{55}$GluThr GluValGlyAspProArgGlyAsnGluLeu AlaGluProGluAlaLys (SEQ ID NO: 34) | Catalyzes the synthesis of hydrouridine, a modified base found in the D-loop of most tRNAs. |

The conversion of arginine amino acid residues to citrulline has several implications for the structure of a protein; for example, the ureido group of citrulline may have a destabilizing effect on protein structure due to its urea-like properties; it may also provoke a conformational change, and may alter the isoelectric point (pI) value and electrophoretic mobility. This destabilizing effect of citrulline has been described on several proteins including filaggrin, trichohyalin and myelin basic protein resulting in a loss of the organized secondary structure of these proteins. Loss of the positive charge associated with citrullination can also be expected to have a large impact on interactions between proteins, modulate signaling potency and interfere with susceptibility to proteolytic degradation. Therefore, this PTM has become an area of interest due to its role in several physiological and pathological processes. Physiological processes include epithelial terminal differentiation, gene expression regulation, and apoptosis. Multiple sclerosis, Alzheimer's disease and Rheumatoid arthritis (RA) are examples of human diseases where protein citrullination involvement has been demonstrated. Protein citrullination may play a role in the progression and development of ischemia/reperfusion injury, myocardial preconditioning or heart failure.

There are five PAD isoforms (PAD1 to PAD4 and PAD6), each encoded by a separate gene. Although the isoforms share a high degree of amino acid sequence homology, they appear to have different tissue-specific expression. RT-PCR or Northern blot analysis revealed that PAD 2 and PAD4 are found in isolated cardiac myocytes (adult) and additionally PAD1 in isolated cardiac fibroblasts (adult) obtained from the heart. PAD1, PAD2 and PAD4 are also present in skeletal muscle but at a higher level than in the heart. This finding suggests that these isoforms are responsible for the deamination of arginine in the heart. As disclosed herein, modulation of the PAD isoforms which are specific to cardiac myocytes and cardiac fibroblasts is possible using interfering RNA (e.g. siRNA) developed against PAD or against a specific isoform. Gene therapy approaches can be used to increase PAD isoforms in target tissues. This can be accomplished using a modified virus or other well established methods for in vivo incorporation of DNA. Specific inhibitors of PAD isoforms can be used to reduce endogenous activity. Further, mutation of the Arg and Cys within the catalytic domain of PAD to Ala or another amino acid residue can be used to reduce enzyme function.

In some embodiments, the peptidyl arginine deiminase isoform (PAD isoform) is selected from isoform 1 (PAD1), isoform 2 (PAD2), isoform 3 (PAD3), isoform 4 (PAD4), and isoform 6 (PAD6).

PAD Inhibitors

There are a number of PAD inhibitors known in the art which are useful in a method to modulate PAD isoform activity. These include without limitation F-amidine [N-α-benzoyl-N5-(2-fluoro-1-iminoethyl)-1-ornithine amide], 2-chloroacetamidine and Cl-amidine[N-α-benzoyl-N5-(2-chloro-1-iminoethyl)-1-ornithine amide].

In various embodiments for use in the methods, kits, and compositions described herein the compound is a PAD inhibitor. In some embodiments, the PAD inhibitor is F-amidine [N-α-benzoyl-N5-(2-fluoro-1-iminoethyl)-1-ornithine amide], 2-chloroacetamidine, or Cl-amidine [N-α-benzoyl-N5-(2-chloro-1-iminoethyl)-1-ornithine amide]. In some embodiments the PAD inhibitor is F-amidine [N-α-benzoyl-N5-(2-fluoro-1-iminoethyl)-1-ornithine amide]. In some embodiments the PAD inhibitor is 2-chloroacetamidine. In some embodiments the PAD inhibitor is Cl-amidine [N-α-benzoyl-N5-(2-chloro-1-iminoethyl)-1-ornithine amide]. In some embodiments the PAD inhibitor is o-F-amidine and o-Cl-amidine [N-α-(2-carboxyl)benzoyl-N5-(2-fluoro-1-iminoethyl)-L-ornithine amide] and [N α-(2-carboxyl)benzoyl-N5-(2-Chloro-1-iminoethyl)-L-ornithine amide]. In some embodiments the PAD inhibitor is a tripeptide (Thr-Asp-F-amidine; TDFA) as a highly selective (up to 65-fold) PAD4 inhibitor. In some embodiments the PAD inhibitor is o-F-amidine [N-α-(2-carboxyl)benzoyl-N5-(2-fluoro-1-iminoethyl)-L-ornithine amide]. In some embodiments the PAD inhibitor is o-Cl-amidine [N α-(2-carboxyl)benzoyl-N5-(2-Chloro-1-iminoethyl)-L-ornithine amide]. In some embodiments the PAD inhibitor is TDF tripeptide (Thr-Asp-F-amidine).

In some embodiments the PAD inhibitor is selected from F-amidine [N-α-benzoyl-N5-(2-fluoro-1-iminoethyl)-1-ornithine amide], 2-chloroacetamidine, Cl-amidine [N-α-benzoyl-N5-(2-chloro-1-iminoethyl)-1-ornithine amide], o-F-amidine [N-α-(2-carboxyl)benzoyl-N5-(2-fluoro-1-iminoethyl)-L-ornithine amide], o-Cl-amidine [N α-(2-carboxyl)benzoyl-N5-(2-Chloro-1-iminoethyl)-L-ornithine amide] and TDF tripeptide (Thr-Asp-F-amidine), or any combination thereof.

In various embodiments the methods, kits, and compositions described herein comprise one or more PAD inhibitors for treating inhibiting, and/or reducing the severity of a cardiovascular disease in a subject.

In various embodiments the methods, kits, and compositions described herein comprise one or more PAD inhibitor for inhibiting the expression or function of Peptidyl Argininedeiminase (PAD).

In various embodiments, the methods, kits, and compositions described herein comprise one or more PAD inhibitors for modulating and/or inhibiting PAD isoform activity.

Citrullinated Proteins and Citrullinated Peptides

In some embodiments, the citrullinated protein for use in the methods, kits and compositions described herein comprises the post-translational conversion of an arginine residue to citrulline.

In some embodiments, the citrullinated peptide for use in the methods, kits and compositions described herein comprises the post-translational conversion of an arginine residue to citrulline.

In some embodiments, the citrullinated proteins for use in the methods, kits and compositions described herein are any one or more or all of myosin heavy chain, myosin binding protein C, tropomyosin α1, tropomyosin α3, actin, titin, lipoprotein lipase, L-lactate dehydrogenase B chain, Alpha-1-antichymotrypsin, Caspase recruitment domain-containing protein 10, Zinc finger ZZ-type and EF-hand domain-containing protein 1, caskin 1 or combination thereof.

In some embodiments, the citrullinated proteins for use in the methods, kits and compositions described herein are any one or more or all of myosin heavy chain, myosin binding protein C, tropomyosin α1, tropomyosin 3, actin, lipoprotein lipase, sulfhydryl oxidase 2, putative zinc finger protein 818, disintegrin and metalloproteinase domain-containing protein 10, titin, Zinc finger ZZ-type and EF-hand domain-containing protein 1, serpin, and tRNA-dihydrouridine synthase.

In some embodiments, the citrullinated proteins for use in the methods, kits and compositions described herein comprise an amino acid sequence selected from SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID. 18.

In some embodiments, the citrullinated proteins for use in the methods, kits and compositions described herein comprise an amino acid sequence selected from SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34.

In some embodiments, the citrullinated peptides for use in the methods, kits and compositions described herein comprise an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, and SEQ ID. 18.

In some embodiments, the citrullinated peptides for use in the methods, kits and compositions described herein comprise an amino acid sequence selected from SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34.

Diagnostic Methods

In various embodiments the present invention provides a method for determining the risk of developing a cardiovascular disease in a subject, comprising: obtaining a sample from the subject; assaying the sample to detect an amount or level of one or more citrullinated proteins or citrullinated peptides; and determining that the subject has increased likelihood of the cardiovascular disease if the amount or level of the citrullinated proteins or citrullinated peptides in the sample is increased relative to a reference sample. In some embodiments, the method further comprises selecting or prescribing a treatment for the subject based on the determination. In some embodiments, the method further comprises treating the subject based on the determination. In some embodiments the method further comprises administering a treatment to the subject based on the determination. In some embodiments the method further comprises providing a treatment to the subject based on the determination. In some embodiments, the method further comprises referring the subject to a specialist based on the determination. In some embodiments the sample is obtained before, during, or after treatment for the disease. In some embodiments the reference sample is obtained from a control subject, wherein the control subject does not have the cardiovascular disease. In some embodiments the reference sample is obtained from a subject that has been successfully treated for the cardiovascular disease. In some embodiments the reference sample is a sample obtained from the subject at an earlier point in time. In some embodiments the treatment comprises administering to the subject a therapeutically effective amount of one or more PAD inhibitors. In some embodiments, the treatment comprises one or more PAD inhibitors.

In various embodiments, the present invention provides a method for determining the risk of developing a cardiovascular disease in a subject, comprising: obtaining a sample from the subject; assaying the sample to detect an amount or level of one or more citrullinated proteins or citrullinated peptides; and determining that the subject has increased likelihood of the cardiovascular disease if the amount or level of the citrullinated proteins or citrullinated peptides in the sample is decreased relative to a reference sample. In some embodiments, the method further comprises selecting or prescribing a treatment for the subject based on the determination. In some embodiments, the method further comprises treating the subject based on the determination. In some embodiments the method further comprises administering a treatment to the subject based on the determination. In some embodiments the method further comprises providing a treatment to the subject based on the determination. In some embodiments, the method further comprises referring the subject to a specialist based on the determination. In some embodiments, the sample is obtained before, during, or after treatment for the disease. In some embodiments, the reference sample is obtained from a control subject, wherein the control subject does not have the cardiovascular disease. In some embodiments, the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for determining the risk of developing a cardiovascular disease in a subject, comprising: obtaining a sample from the subject; assaying the sample to detect an amount or level of one or more citrullinated proteins or citrullinated peptides; and determining that the subject has increased likelihood of the cardiovascular disease if the amount or level of the citrullinated proteins or citrullinated peptides in the sample is changed relative to a reference sample. In some embodiments, the method further comprises selecting or prescribing a treatment for the subject based on the determination. In some embodiments, the method further comprises treating the subject based on the determination. In some embodiments, the method further comprises administering a treatment to the subject based on the determination. In some embodiments, the method further comprises providing a treatment to the subject based on the determination. In some embodiments, the method further comprises referring the subject to a specialist based on the determination. In some embodiments the sample is obtained before, during, or after treatment for the disease. In some embodiments, the reference sample is obtained from a control subject, wherein the control subject does not have the cardiovascular disease. In some embodiments, the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for determining the risk of developing a cardiovascular disease in a subject, comprising: obtaining a sample from the subject; assaying the sample to detect an amount or level of one or more citrullinated amino acids and/or citrullinated amino acid residues in a citrullinated protein or citrullinated peptide; and determining that the subject has increased likelihood of the cardiovascular disease if the amount or level of the citrullinated amino acids and/or citrullinated amino acid residues in the citrullinated protein or citrullinated peptide in the sample is increased relative to a reference sample. In some embodiments, the method further comprises selecting or prescribing a treatment for the subject based on the determination. In some embodiments, the method further comprises treating the subject based on the determination. In some embodiments, the method further comprises administering a treatment to the subject based on the determination. In some embodiments, the method further comprises providing a treatment to the subject based on the determination. In some embodiments, the method further comprises referring the subject to a specialist based on the determination. In some embodiments, the sample is obtained before, during, or after treatment for the disease. In some embodiments, the reference sample is obtained from a control subject, wherein the control subject does not have the cardiovascular disease. In some embodiments, the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for determining the risk of developing a cardiovascular disease in a subject, comprising: obtaining a sample from the subject; assaying the sample to detect an amount or level of one or more citrullinated amino acids or citrullinated amino acid residues in a citrullinated protein or citrullinated peptide; and determining that the subject has increased likelihood of the cardiovascular disease if the amount or level of the citrullinated amino acids or citrullinated amino acid residues in the citrullinated protein or citrullinated peptide in the sample is decreased relative to a reference sample. In some embodiments, the method further comprises selecting or prescribing a treatment for the subject based on the determination. In some embodiments, the method further comprises treating the subject based on the determination. In some embodiments, the method further comprises administering a treatment to the subject based on the determination. In some embodiments, the method further comprises providing a treatment to the subject based on the determination. In some embodiments, the method further comprises referring the subject to a specialist based on the determination. In some embodiments, the sample is obtained before, during, or after treatment for the disease. In some embodiments, the reference sample is obtained from a control subject, wherein the control subject does not have the cardiovascular disease. In some embodiments the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for determining the risk of developing a cardiovascular disease in a subject, comprising: obtaining a sample from the subject; assaying the sample to detect an amount or level of one or more citrullinated amino acids or citrullinated amino acid residues in a citrullinated protein or citrullinated peptide; and determining that the subject has increased likelihood of the cardiovascular disease if the amount or level of the citrullinated amino acids or citrullinated amino acid residues in the citrullinated protein or citrullinated peptide in the sample is changed relative to a reference sample. In some embodiments, the method further comprises selecting or prescribing a treatment for the subject based on the determination. In some embodiments, the method further comprises treating the subject based on the determination. In some embodiments, the method further comprises administering a treatment to the subject based on the determination. In some embodiments, the method further comprises providing a treatment to the subject based on the determination. In some embodiments, the method further comprises referring the subject to a specialist based on the determination. In some embodiments, the sample is obtained before, during, or after treatment for the disease. In some embodiments, the reference sample is obtained from a control subject, wherein the control subject does not have the cardiovascular disease. In some embodiments, the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments the present invention provides a method for selecting a subject for a treatment or a therapy that inhibits one or more peptidyl arginine deiminase isoforms, comprising: obtaining a sample from the subject; assaying the sample to determine an amount or level of one or more citrullinated proteins or citrullinated peptides; and selecting the subject for the treatment or the therapy that inhibits the peptidyl arginine deiminase isoforms if the amount or level of the citrullinated proteins or citrullinated peptides is increased relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for selecting a subject for a treatment or a therapy that inhibits one or more peptidyl arginine deiminase isoforms, comprising: obtaining a sample from the subject; assaying the sample to determine an amount or level of one or more citrullinated proteins or citrullinated peptides; and selecting the subject for the treatment or the therapy that inhibits the peptidyl arginine deiminase isoforms if the amount or level of the citrullinated proteins or citrullinated peptides is decreased relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for selecting a subject for a treatment or a therapy that inhibits one or more peptidyl arginine deiminase isoforms, comprising: obtaining a sample from the subject; assaying the sample to determine an amount or level of one or more citrullinated proteins or citrullinated peptides; and selecting the subject for the treatment or the therapy that inhibits the peptidyl arginine deiminase isoforms if the amount or level of the citrullinated proteins or citrullinated peptides is changed relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for selecting a subject for a treatment or a therapy that inhibits one or more peptidyl arginine deiminase isoforms, comprising: obtaining a sample from the subject; assaying the sample to determine an amount or level of one or more citrullinated amino acids or citrullinated amino acid residues in a citrullinated protein or citrullinated peptide; and selecting the subject for the treatment or the therapy that inhibits the peptidyl arginine deiminase isoforms if the amount or level of the citrullinated amino acids or citrullinated amino acid residues in the citrullinated protein or citrullinated peptide is increased relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments the present invention provides a method for selecting a subject for a treatment or a therapy that inhibits one or more peptidyl arginine deiminase isoforms, comprising: obtaining a sample from the subject; assaying the sample to determine an amount or level of one or more citrullinated amino acids or citrullinated amino acid residues in a citrullinated protein or citrullinated peptide; and selecting the subject for the treatment or the therapy that inhibits the peptidyl arginine deiminase isoforms if the amount or level of the citrullinated amino acids or citrullinated amino acid residues in the citrullinated protein or citrullinated peptide is decreased relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments, the present invention provides a method for selecting a subject for a treatment or a therapy that inhibits one or more peptidyl arginine deiminase isoforms, comprising: obtaining a sample from the subject; assaying the sample to determine an amount or level of one or more citrullinated amino acids or citrullinated amino acid residues in a citrullinated protein or citrullinated peptide; and selecting the subject for the treatment or the therapy that inhibits the peptidyl arginine deiminase isoforms if the amount or level of the citrullinated amino acids or citrullinated amino acid residues in the citrullinated protein or citrullinated peptide is changed relative to a reference sample. In some embodiments, the method further comprises selecting or prescribing a treatment based on the determination. In some embodiments, the method further comprises treating the subject based on the determination. In some embodiments, the method further comprises administering a treatment to the subject. In some embodiments, the method further comprises referring the subject to a specialist. In some embodiments, the sample is obtained before, during, or after treatment for the disease. In some embodiments, the reference sample is obtained from a control subject, wherein the control subject does not have cardiovascular disease. In some embodiments, the reference sample is obtained from a subject that has been successfully treated for the disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of cardiovascular disease in the subject; and selecting and/or prescribing a treatment for the subject based on the diagnosis. In some embodiments, the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of or is a diagnosis of cardiovascular disease in the subject.

In various embodiments the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of or is a diagnosis of cardiovascular disease in the subject.

In various embodiments the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of or is a diagnosis of cardiovascular disease in the subject. In some embodiments, the method further comprises selecting or prescribing a treatment for the subject based on the diagnosis. In some embodiments, the method further comprises treating the subject based on the diagnosis. In some embodiments, the method further comprises administering a treatment to the subject based on the diagnosis. In some embodiments, the method further comprises providing a treatment to the subject based on the diagnosis. In some embodiments, the method further comprises referring the subject to a specialist based on the diagnosis. In some embodiments, the sample is obtained before, during, or after treatment for the disease. In some embodiments, the reference sample is obtained from a control subject, wherein the control subject does not have the cardiovascular disease. In some embodiments, the reference sample is obtained from a subject that has been successfully treated for the cardiovascular disease. In some embodiments, the reference sample is a sample obtained from the subject at an earlier point in time. In some embodiments, the treatment comprises administering to the subject a therapeutically effective amount of one or more PAD inhibitors. In some embodiments, the treatment comprises one or more PAD inhibitors.

In various embodiments the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of cardiovascular disease in the subject; and selecting and/or prescribing a treatment for the subject based on the diagnosis. In some embodiments, the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of cardiovascular disease in the subject; and selecting and/or prescribing a treatment for the subject based on the diagnosis. In some embodiments, the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and selecting and/or prescribing a treatment for the subject based on the diagnosis. In some embodiments, the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or citrullinated amino acid residues from the reference sample is indicative of or is a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an decrease in the amount or level of the citrullinated amino acids or citrullinated amino acid residues in the sample from the subject relative to the amount or level of the citrullinated amino acids or citrullinated amino acid residues from the reference sample is indicative of or is a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or citrullinated amino acid residues from the reference sample is indicative of or is a diagnosis of cardiovascular disease in the subject. In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an decrease in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and selecting and/or prescribing a treatment for the subject based on the diagnosis. In some embodiments the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and selecting and/or prescribing a treatment for the subject based on the diagnosis. In some embodiments, the method further comprises administering a treatment to the subject. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of the efficacy of the treatment. In some embodiments the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of the efficacy of the treatment. In some embodiments the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of the efficacy of the treatment. In some embodiments the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or amino acid residues from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated amino acids or citrullinated amino acid residues in the citrullinated protein or citrullinated peptide in the sample from the subject to an amount or level of one or more citrullinated amino acids or citrullinated amino acid residues in the citrullinated protein or citrullinated peptide from a reference sample, wherein a decrease in the amount or level of the citrullinated amino acids or citrullinated amino acid residues in the sample from the subject relative to the amount or level of the citrullinated amino acids or citrullinated amino acid residues from the reference sample is indicative of the efficacy of the treatment. In some embodiments the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or amino acid residues from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an decrease in the amount or level of the citrullinated amino acids or citrullinated amino acid residues in the sample from the subject relative to the amount or level of the citrullinated amino acids or amino acid residues from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; and comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or amino acid residues from the reference sample is indicative of or a diagnosis of cardiovascular disease in the subject. In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an decrease in the amount or level of the citrullinated amino acids or citrullinated amino acid residues in the sample from the subject relative to the amount or level of the citrullinated amino acids or amino acid residues from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated amino acids or citrullinated amino acid residues in the citrullinated protein or citrullinated peptide in the sample from the subject to an amount or level of one or more citrullinated amino acids or citrullinated amino acid residues in the citrullinated protein or citrullinated peptide from a reference sample, wherein an increase in the amount or level of the citrullinated amino acids or citrullinated amino acid residues in the sample from the subject relative to the amount or level of the citrullinated amino acids or citrullinated amino acid residues from the reference sample is indicative of the efficacy of the treatment. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or amino acid residues from the reference sample is indicative of cardiovascular disease in the subject; and treating the subject and/or administering a treatment to the subject based on the diagnosis. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease. In some embodiments, the method further comprises assessing the efficacy of the treatment, comprising: comparing the amount or level of the citrullinated amino acids or citrullinated amino acid residues in the citrullinated protein or citrullinated peptide in the sample from the subject to an amount or level of one or more citrullinated amino acids or citrullinated amino acid residues in the citrullinated protein or citrullinated peptide from a reference sample, wherein a change in the amount or level of the citrullinated amino acids or citrullinated amino acid residues in the sample from the subject relative to the amount or level of the citrullinated amino acids or citrullinated amino acid residues from the reference sample is indicative of the efficacy of the treatment. In some embodiments, the treatment comprises administering to the subject a therapeutically effective amount of one or more PAD inhibitors. In some embodiments, the treatment comprises one or more PAD inhibitors.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of cardiovascular disease in the subject; and referring the subject to a specialist. In some embodiments the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated proteins or citrullinated peptides in the sample from the subject; and comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of or a diagnosis of cardiovascular disease in the subject. In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of cardiovascular disease in the subject; and referring the subject to a specialist. In some embodiments, the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method for diagnosing cardiovascular disease in a subject, comprising: obtaining a sample from the subject; detecting an amount or level of one or more citrullinated proteins or citrullinated peptides in the sample from the subject; comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of cardiovascular disease in the subject; and referring the subject to a specialist. In some embodiments, the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and referring the subject to a specialist. In some embodiments, the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein an increase in the amount or level of the citrullinated amino acids or citrullinated amino acid residues in the sample from the subject relative to the amount or level of the citrullinated amino acids or citrullinated amino acid residues from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a decrease in the amount or level of the citrullinated amino acids or citrullinated amino acid residues in the sample from the subject relative to the amount or level of the citrullinated amino acids or citrullinated amino acid residues from the reference sample is indicative of or a diagnosis of cardiovascular disease in the subject. In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or citrullinated amino acid residues from the reference sample is indicative of or a diagnosis of cardiovascular disease in the subject. In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a decrease in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and referring the subject to a specialist. In some embodiments, the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method for diagnosing cardiovascular disease in a subject, comprising: obtaining a sample from the subject; detecting an amount or level of one or more citrullinated amino acids or citrullinated amino acid residues in a citrullinated protein or citrullinated peptide in the sample from the subject; comparing the amount or level of the citrullinated amino acids or citrullinated amino acid residues in the citrullinated protein or citrullinated peptide in the sample from the subject to an amount or level of one or more citrullinated amino acids or citrullinated amino acid residues in a citrullinated protein or citrullinated peptide from a reference sample, wherein a change in the amount or level of the citrullinated amino acids or citrullinated amino acid residues in the sample from the subject relative to the amount or level of the citrullinated amino acids or citrullinated amino acid residues from the reference sample is indicative of cardiovascular disease in the subject; and referring the subject to a specialist. In some embodiments, the specialist is a cardiovascular physician, a heart failure physician, a cardiologist, a vascular physician, an electrophysiologist, a cardiovascular surgeon, an interventional physician, an imaging physician, a preventive cardiologist, a cardiothoracic surgeon, or a vascular surgeon. In some embodiments the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method of diagnosing and/or prognosing a cardiovascular disease in a subject, comprising: obtaining a sample from the subject; measuring one or more citrullinated proteins or citrullinated peptides in the sample so as to obtain a biomarker signature for the subject; comparing the biomarker signature from the subject to a plurality of reference biomarker signatures; diagnosing and/or prognosing the cardiovascular disease of the subject based on the comparison; and treating the subject and/or administering a treatment and/or selecting a treatment and/or prescribing a treatment and/or providing a treatment and/or selecting a preventative treatment and/or prescribing a preventative treatment and/or providing a preventative treatment and/or administering a preventative treatment. In some embodiments, the treatment comprises administering to the subject a therapeutically effective amount of one or more PAD inhibitors. In some embodiments, the treatment comprises one or more PAD inhibitors.

In some embodiments, the plurality of reference biomarker signatures are from a plurality of subjects having one or more cardiovascular diseases. In some embodiments, the plurality of reference biomarker signatures are from a plurality of healthy subjects. In some embodiments, the subject is diagnosed and/or prognosed with having a cardiovascular disease if the comparison of the biomarker signature from the subject to a plurality of reference biomarker signatures shows a change or difference in the biomarker signature from the subject relative to a plurality of reference biomarker signatures.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of the efficacy of the treatment.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of the efficacy of the treatment.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of the efficacy of the treatment.

In some embodiments, the method further comprises assessing the efficacy of the treatment, comprising: comparing the amount or level of one or more citrullinated amino acids or citrullinated amino acid residues in the citrullinated proteins or citrullinated peptides in the sample from the subject to an amount or level of one or more citrullinated amino acids or citrullinated amino acid residues in the citrullinated proteins or citrullinated peptides from a reference sample, wherein a decrease in the amount or level of the citrullinated amino acids or citrullinated amino acid residues in the citrullinated proteins or citrullinated peptides in the sample from the subject relative to the amount or level of the citrullinated amino acids or citrullinated amino acid residues in the citrullinated proteins or citrullinated peptides from the reference sample is indicative of the efficacy of the treatment.

In some embodiments, the method further comprises assessing the efficacy of the treatment, comprising: comparing the amount or level of one or more citrullinated amino acids or citrullinated amino acid residues in the citrullinated proteins or citrullinated peptides in the sample from the subject to an amount or level of one or more citrullinated amino acids or citrullinated amino acid residues in the citrullinated proteins or citrullinated peptides from a reference sample, wherein an increase in the amount or level of the citrullinated amino acids or citrullinated amino acid residues in the citrullinated proteins or citrullinated peptides in the sample from the subject relative to the amount or level of the citrullinated amino acids or citrullinated amino acid residues in the citrullinated proteins or citrullinated peptides from the reference sample is indicative of the efficacy of the treatment.

In some embodiments, the method further comprises assessing the efficacy of the treatment, comprising: comparing the amount or level of one or more citrullinated amino acids or citrullinated amino acid residues in the citrullinated proteins or citrullinated peptides in the sample from the subject to an amount or level of one or more citrullinated amino acids or citrullinated amino acid residues in the citrullinated proteins or citrullinated peptides from a reference sample, wherein a change in the amount or level of the citrullinated amino acids or citrullinated amino acid residues in the citrullinated proteins or citrullinated peptides in the sample from the subject relative to the amount or level of the citrullinated amino acids or citrullinated amino acid residues in the citrullinated proteins or citrullinated peptides from the reference sample is indicative of the efficacy of the treatment.

In various embodiments, the present invention provides a method of diagnosing and/or prognosing a cardiovascular disease in a subject, comprising: obtaining a sample from the subject; measuring and/or detecting the presence of one or more citrullinated proteins or citrullinated peptides in the sample so as to obtain a biomarker signature for the subject; comparing the biomarker signature from the subject to a plurality of reference biomarker signatures; and diagnosing and/or prognosing the cardiovascular disease of the subject based on the comparison. In various embodiments the present invention provides a method of diagnosing and/or prognosing a cardiovascular disease in a subject, comprising: obtaining a sample from the subject; measuring and/or detecting one or more citrullinated proteins or citrullinated peptides in the sample so as to obtain a biomarker signature for the subject; comparing the biomarker signature from the subject to a plurality of reference biomarker signatures; and diagnosing and/or prognosing the cardiovascular disease of the subject based on the comparison. In some embodiments, the method further comprises referring the subject to a specialist. In some embodiments, the method further comprises, selecting and/or prescribing and/or providing and/or administering a treatment and/or a preventative treatment to the subject. In some embodiments, the treatment comprises administering to the subject a therapeutically effective amount of one or more PAD inhibitors. In some embodiments, the treatment comprises one or more PAD inhibitors.

In some embodiments, the method further comprises treating the subject and/or administering a treatment and/or selecting a treatment and/or prescribing a treatment and/or providing a treatment and/or selecting a preventative treatment and/or prescribing a preventative treatment and/or providing a preventative treatment and/or administering a preventative treatment.

In some embodiments, the method further comprises selecting and/or prescribing a treatment for the subject based on the diagnosis. In some embodiments, the method further comprises administering a treatment to the subject. In some embodiments, the method further comprises referring the subject to a specialist based on the diagnosis.

In various embodiments, the present invention provides a method of diagnosing and/or prognosing a cardiovascular disease in a subject, comprising: obtaining a sample from the subject; measuring and/or detecting the presence of one or more citrullinated amino acids or citrullinated amino acid residues of a citrullinated protein or citrullinated peptide in the sample so as to obtain a biomarker signature for the subject; comparing the biomarker signature from the subject to a plurality of reference biomarker signatures; and diagnosing and/or prognosing the cardiovascular disease of the subject based on the comparison. In various embodiments the present invention provides a method of diagnosing and/or prognosing a cardiovascular disease in a subject, comprising: obtaining a sample from the subject; detecting and/or measuring the presence of one or more citrullinated proteins or citrullinated peptides in the sample, wherein the presence of one or more citrullinated proteins or citrullinated peptides in the sample is indicative of or is a diagnosis of cardiovascular disease. In various embodiments the present invention provides a method of diagnosing and/or prognosing a cardiovascular disease in a subject, comprising: obtaining a sample from the subject; detecting and/or measuring the presence of one or more citrullinated amino acids or citrullinated amino acid residues in a citrullinated protein or citrullinated peptide in the sample, wherein the presence of one or more one or more citrullinated amino acids or citrullinated amino acid residues in the citrullinated protein or citrullinated peptide in the sample is indicative of or is a diagnosis of cardiovascular disease.

In some embodiments, the presence of and/or measuring and/or detecting and/or measuring the presence of and/or detecting the presence of and/or detecting an amount or level of and/or measuring an amount or level of the citrullinated protein or citrullinated peptide and or citrullinated amino acid or citrullinated amino acid residue is detected and/or measured and/or performed and/or obtained using mass spectrometry, high resolution mass spectrometry, tandem mass spectrometry, binding assay, immunoassay, antibody binding or immunohistochemistry.

In various embodiments, the present invention provides a method of diagnosing cardiovascular disease in a subject, comprising (a) obtaining a biological sample from said subject, and (b) detecting the presence of a citrullinated protein in the biological sample obtained from said subject, wherein the level of citrullinated protein is indicative of cardiovascular disease. In some embodiments, the citrullinated protein is elevated compared to the control amount of the citrullinated protein. In some embodiments, the biological sample is selected from the group consisting of blood, plasma, serum and tissue biopsy. In some embodiments, the tissue biopsy is myocardial tissue. In some embodiments, the citrullinated protein comprises the post-translational conversion of an arginine residue to citrulline. In some embodiments, the citrullinated protein is selected from the group consisting of myosin heavy chain, myosin binding protein C, tropomyosin α1, tropomyosin α3, actin, titin, lipoprotein lipase, L-lactate dehydrogenase B chain, Alpha-1-antichymotrypsin, Caspase recruitment domain-containing protein 10, Zinc finger ZZ-type and EF-hand domain-containing protein 1. In some embodiments, the citrullinated protein comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17. In some embodiments, the citrullinated protein comprises an amino acid sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34. In some embodiments, the presence of the citrullinated protein is detected using mass spectrometry, high resolution mass spectrometry, tandem mass spectrometry, binding assay, immunoassay, antibody binding or immunohistochemistry.

In various embodiments, the present invention provides a method of diagnosing susceptibility to autoimmunity to citrullinated proteins in a subject, comprising (a) obtaining a biological sample from said subject, and (b) detecting the presence of a citrullinated protein in the biological sample obtained from said subject, wherein the level of citrullinated protein is indicative of cardiovascular disease. In some embodiments, the citrullinated protein is elevated compared to the control amount of the citrullinated protein. In some embodiments, the biological sample is selected from the group consisting of blood, plasma, serum and tissue biopsy. In some embodiments, the tissue biopsy is myocardial tissue. In some embodiments, the citrullinated protein comprises the conversion of an arginine residue to citrulline. In some embodiments, the citrullinated protein is selected from the group consisting of myosin heavy chain, myosin binding protein C, tropomyosin α1, tropomyosin α3, actin, titin, lipoprotein lipase, L-lactate dehydrogenase B chain, Alpha-1-antichymotrypsin, Caspase recruitment domain-containing protein 10, Zinc finger ZZ-type and EF-hand domain-containing protein 1. In some embodiments, the citrullinated protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17. In some embodiments, the citrullinated protein comprises an amino acid sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34. In some embodiments, the presence of the citrullinated protein is detected using mass spectrometry, high resolution mass spectrometry, tandem mass spectrometry, binding assay, immunoassay, antibody binding or immunohistochemistry.

In various embodiments, the present invention provides a method of modulating the activity of peptidyl arginine deiminase isoform 1 (PAD1), isoform 2 (PAD2) and/or isoform 4 (PAD4), by administering to a subject in need thereof, an inhibitor of PAD activity. In some embodiments, the inhibitor is selected from the group consisting of F-amidine [N-α-benzoyl-N5-(2-fluoro-1-iminoethyl)-1-ornithine amide], 2-chloroacetamidine and Cl-amidine[N-α-benzoyl-N5-(2-chloro-1-iminoethyl)-1-ornithine amide].

Treatment Methods

In various embodiments, the present invention provides a method for treating, inhibiting, and/or reducing the severity of a cardiovascular disease in a subject, comprising: selecting a subject diagnosed with one or more cardiovascular diseases by the methods described herein and administering to the subject a therapeutically effective amount of one or more PAD inhibitors so as to treat, inhibit, and/or reduce the severity of the cardiovascular disease.

In various embodiments the present invention provides a method for treating, inhibiting, and/or reducing the severity of a cardiovascular disease in a subject, comprising: providing one or more PAD inhibitors; selecting a subject diagnosed with one or more cardiovascular diseases by the methods described herein; and administering to the subject a therapeutically effective amount of the PAD inhibitors so as to treat, inhibit, and/or reduce the severity of the cardiovascular disease.

In some embodiments, the one or more cardiovascular diseases are associated with activity of one or more peptidyl arginine deiminase isoforms in the subject. In some embodiments, the one or more cardiovascular diseases are associated with increased amounts or levels of citrullinated proteins or citrullinated peptides in the subject compared to a reference sample. In some embodiments, the one or more cardiovascular diseases are associated with decreased amounts or levels of citrullinated proteins or citrullinated peptides in the subject compared to a reference sample. In some embodiments, the one or more cardiovascular diseases are associated with a change in amounts or levels of citrullinated proteins or citrullinated peptides in the subject compared to a reference sample. In some embodiments, the one or more cardiovascular diseases are associated with the presence of one or more citrullinated proteins or citrullinated peptides in the subject.

In some embodiments, the one or more cardiovascular diseases are associated with increased amounts or levels of citrullinated amino acids or citrullinated amino acid residues in a citrullinated protein or citrullinated peptide in a subject compared to a reference sample. In some embodiments, the one or more cardiovascular diseases are associated with decreased amounts or levels of citrullinated amino acids or citrullinated amino acid residues in a citrullinated protein or citrullinated peptide in a subject compared to a reference sample. In some embodiments, the one or more cardiovascular diseases are associated with a change in amounts or levels of citrullinated amino acid or citrullinated amino acid residues in a citrullinated protein or citrullinated peptide in a subject compared to a reference sample.

In some embodiments, the one or more cardiovascular diseases are associated with an increase in an amount or level of one or more citrullinated amino acids or citrullinated amino acid residues in a citrullinated protein or citrullinated peptide in a subject compared to a reference sample. In some embodiments, the one or more cardiovascular diseases are associated with a decrease in an amount or level of one or more citrullinated amino acids or citrullinated amino acid residues in a citrullinated protein or citrullinated peptide in a subject compared to a reference sample. In some embodiments, the one or more cardiovascular diseases are associated with a change in an amount or level of citrullinated amino acids or citrullinated amino acid residues in a citrullinated protein or citrullinated peptide in a subject compared to a reference sample.

In some embodiments, the one or more cardiovascular diseases are associated with an increase in an amount or level of one or more citrullinated proteins or citrullinated peptides in a subject compared to a reference sample. In some embodiments, the one or more cardiovascular diseases are associated with a decrease in an amount or level of one or more citrullinated proteins or citrullinated peptides in a subject compared to a reference sample. In some embodiments, the one or more cardiovascular diseases are associated with a change in an amount or level of one or more citrullinated proteins or citrullinated peptides in a subject compared to a reference sample.

In some embodiments, the PAD inhibitors are administered in the form of a pharmaceutical composition.

In some embodiments, the citrullinated protein is any one or more or all of myosin heavy chain, myosin binding protein C, tropomyosin α1, tropomyosin α3, actin, titin, lipoprotein lipase, L-lactate dehydrogenase B chain, Alpha-1-antichymotrypsin, Caspase recruitment domain-containing protein 10, Zinc finger ZZ-type EF-hand domain-containing protein 1, and caskin 1.

In some embodiments, the citrullinated protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO. 18.

In some embodiments, the citrullinated protein is any one or more or all of myosin heavy chain, myosin binding protein C, tropomyosin α1, tropomyosin 3, actin, lipoprotein lipase, sulfhydryl oxidase 2, putative zinc finger protein 818, disintegrin and metalloproteinase domain-containing protein 10, titin, Zinc finger ZZ-type and EF-hand domain-containing protein 1, serpin, and tRNA-dihydrouridine synthase.

In some embodiments, the citrullinated protein comprises an amino acid sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34.

In some embodiments the citrullinated peptides for use in the methods, kits and compositions described herein comprise an amino acid sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID. 18.

In some embodiments the citrullinated peptides for use in the methods, kits and compositions described herein comprise an amino acid sequence selected from SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34.

In various embodiments, the present invention provides a method for treating, inhibiting, and/or reducing the severity of cardiovascular disease associated with increased amounts or levels of Neutrophil Extracellular Traps (NETs) in a subject, comprising: selecting a subject who has cardiovascular disease associated with increased amounts or levels of Neutrophil Extracellular Traps (NETs); and administering to the subject a therapeutically effective amount of one or more PAD inhibitors to treat, inhibit, and/or reduce the severity of the cardiovascular disease associated with increased amounts or levels of Neutrophil Extracellular Traps (NETs). In some embodiments, the method further comprises providing one or more PAD inhibitors. In some embodiments, the method further comprises assessing the efficacy of the treatment, comprising: comparing the amount or level of the Neutrophil Extracellular Traps (NETs) in the sample from the subject to an amount or level of Neutrophil Extracellular Traps (NETs) from a reference sample, wherein a decrease in the amount or level of the Neutrophil Extracellular Traps (NETs) in the sample from the subject relative to the amount or level of the Neutrophil Extracellular Traps (NETs) from the reference sample is indicative of the efficacy of the treatment. In some embodiments, the subject or a sample from the subject has increased amounts or levels of Neutrophil Extracellular Traps (NETs) compared to amount or levels of Neutrophil Extracellular Traps (NETs) in a reference sample.

In some embodiments, the reference sample is obtained from a control subject, wherein the control subject does not have a cardiovascular disease. In some embodiments, the reference sample is obtained from the subject before the subject is treated for the disease. In some embodiments, the reference sample is from a subject that has been successfully treated for the disease.

In various embodiments, the present invention provides a method of treating, inhibiting, and/or reducing the severity of a cardiovascular disease in a subject, comprising: obtaining a sample from the subject; measuring an expression level of one or more citrullinated proteins in the sample; comparing the citrullinated protein expression levels in the sample from the subject to one or more citrullinated protein expression levels in a reference sample, wherein an increase in the citrullinated protein expression levels in the sample from the subject relative to the citrullinated protein expression levels from the reference sample is a diagnosis of cardiovascular disease in the subject; and selecting, prescribing, and/or administering a treatment and/or therapy to the subject based on the diagnosis, wherein the treatment and/or therapy comprises administering to the subject a therapeutically effective amount of one or more PAD inhibitors so as to treat the cardiovascular disease. In some embodiments, the citrullinated protein was myosin heavy chain. In some embodiments, the cardiovascular disease is heart failure.

In various embodiments, the present invention provides a method of treating, inhibiting, and/or reducing the severity of a cardiovascular disease in a subject, comprising: obtaining a sample from the subject; measuring an expression level of one or more citrullinated proteins in the sample; comparing the citrullinated protein expression levels in the sample from the subject to one or more citrullinated protein expression levels in a reference sample, wherein an decrease in the citrullinated protein expression levels in the sample from the subject relative to the citrullinated protein expression levels from the reference sample is a diagnosis of cardiovascular disease in the subject; and selecting, prescribing, and/or administering a treatment and/or therapy to the subject based on the diagnosis, wherein the treatment and/or therapy comprises administering to the subject a therapeutically effective amount of one or more PAD inhibitors so as to treat the cardiovascular disease. In some embodiments, the citrullinated protein was actin. In some embodiments, the cardiovascular disease is heart failure.

In various embodiments, the present invention provides a method of treating, inhibiting, and/or reducing the severity of a cardiovascular disease in a subject, comprising: obtaining a sample from the subject; measuring an expression level of one or more citrullinated proteins in the sample; comparing the citrullinated protein expression levels in the sample from the subject to one or more citrullinated protein expression levels in a reference sample, wherein a change in the citrullinated protein expression levels in the sample from the subject relative to the citrullinated protein expression levels from the reference sample is a diagnosis of cardiovascular disease in the subject; and selecting, prescribing, and/or administering a treatment and/or therapy to the subject based on the diagnosis, wherein the treatment and/or therapy comprises administering to the subject a therapeutically effective amount of one or more PAD inhibitors so as to treat the cardiovascular disease.

In some embodiments, the method further comprises assessing the efficacy of the treatment, comprising: comparing the citrullinated protein expression levels in the sample from the subject to citrullinated protein expression levels from a reference sample, wherein a decrease in the citrullinated protein expression levels in the sample from the subject relative to the citrullinated protein expression levels from the reference sample is indicative of the efficacy of the treatment.

In some embodiments, the method further comprises assessing the efficacy of the treatment, comprising: comparing the citrullinated protein expression levels in the sample from the subject to citrullinated protein expression levels from a reference sample, wherein an increase in the citrullinated protein expression levels in the sample from the subject relative to the citrullinated protein expression levels from the reference sample is indicative of the efficacy of the treatment.

In some embodiments, the method further comprises assessing the efficacy of the treatment, comprising: comparing the citrullinated protein expression levels in the sample from the subject to citrullinated protein expression levels from a reference sample, wherein a change in the citrullinated protein expression levels in the sample from the subject relative to the citrullinated protein expression levels from the reference sample is indicative of the efficacy of the treatment.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a decrease in the amount or level of the citrullinated proteins or citrullinated peptides in the sample from the subject relative to the amount or level of the citrullinated proteins or citrullinated peptides from the reference sample is indicative of the efficacy of the treatment.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein an increase in the amount or level of the citrullinated proteins or citrullinated peptides in the sample from the subject relative to the amount or level of the citrullinated proteins or citrullinated peptides from the reference sample is indicative of the efficacy of the treatment.

In some embodiments, the method further comprises assessing the efficacy of the treatment, comprising: comparing the amount or level of the citrullinated proteins or citrullinated peptides in the sample from the subject to an amount or level of one or more citrullinated proteins or citrullinated peptides from a reference sample, wherein a change in the amount or level of the citrullinated proteins or citrullinated peptides in the sample from the subject relative to the amount or level of the citrullinated proteins or citrullinated peptides from the reference sample is indicative of the efficacy of the treatment.

Dosages

In various embodiments, the amount of one or more compounds that can be combined with the carrier material to produce a single dosage form will generally be that amount of the compounds that produces a therapeutic effect. Generally, out of one hundred percent, this amount will range from about 0.01% to 99% of compound. In some embodiments, out of one hundred percent, this amount will range from about 5% to about 70%. In some embodiments, out of one hundred percent, this amount will range from 10% to about 30%. In some embodiments, the compound is one or more PAD inhibitors.

The dosage can be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like. In some embodiments, the compound is one or more PAD inhibitors.

In some embodiments, the compositions are administered at a dosage so that one or more compounds or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration. In some embodiments, the compound is one or more PAD inhibitors.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compounds. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. In some embodiments, the compound is one or more PAD inhibitors.

In some embodiments, the therapeutically effective amount of the compound is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day. In some embodiments, the compound is one or more PAD inhibitors.

In some embodiments, the compound is administered to the subject 1-3 times per day or 1-7 times per week. In some embodiments, the compound is one or more PAD inhibitors.

In some embodiments, the compound is administrated to the subject for 1-5 days, 1-5 weeks, 1-5 months, or 1-5 years. In some embodiments, the compound is one or more PAD inhibitors.

Modes of Administration

As used herein, the term "administering," refers to the placement of one or more compounds or a composition comprising one or more compounds as disclosed herein into a subject by a method or route which results in at least partial localization of the compound or composition thereof at a desired site such that a desired effect is produced. Routes of administration suitable for the methods of the invention include both local and systemic administration. Generally, local administration results in more of the compounds or composition thereof being delivered to a specific location as compared to the entire body of the subject, whereas, systemic administration results in delivery to essentially the entire body of the subject. In some embodiments, the compound is one or more PAD inhibitors.

"Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intravascular, intravenous, intraarterial, subarachnoid, subcapsular, subcutaneous, transmucosal, or transtracheal. Via the parenteral route, the compound may be in the form of solutions or suspensions for infusion or for injection, or as lyophilized powders. Via the enteral route, the compound can be in the form of capsules, gel capsules, tablets, sugar-coated tablets, syrups, suspensions, solutions, powders, granules, emulsions, microspheres, nanoparticles comprised of proteineous or non-proteineous components or nanospheres or lipid vesicles or polymer vesicles allowing controlled release. Via the topical route, the compound can be in the form of aerosol, lotion, cream, gel, ointment, suspensions, solutions or emulsions. In an embodiment, the compound may be provided in a powder form and mixed with a liquid, such as water, to form a beverage. In accordance with the present invention, "administering" can be self-administering. For example, it is considered as "administering" that a subject consumes one or more compounds as disclosed herein. In some embodiments, the compound is one or more PAD inhibitors.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the various aspects described herein, the one or more compounds or compositions thereof are administered by intravenous infusion or injection. In some embodiments, the compound is one or more PAD inhibitors.

Patient Populations

In various embodiments, the subject is diagnosed with one or more cardiovascular diseases. In some embodiments, the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof. In some embodiments, the cardiovascular disease is selected from ischemic heart disease, cardiomyopathy, hypertensive heart disease, and heart failure, or any combination thereof. In some embodiments, the subject is human and is diagnosed with one or more cardiovascular diseases.

In various embodiments, the subject is at risk of developing one or more cardiovascular diseases. In some embodiments, the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof. In some embodiments, the cardiovascular disease is selected from ischemic heart disease, cardiomyopathy, hypertensive heart disease, and heart failure, or any combination thereof. In some embodiments, the subject is human and is at risk of developing one or more cardiovascular diseases.

In various embodiments, the subject has one or more cardiovascular diseases. In some embodiments, the cardiovascular disease is selected from congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof. In some embodiments, the cardiovascular disease is selected from ischemic heart disease, cardiomyopathy, hypertensive heart disease, and heart failure, or any combination thereof. In some embodiments, the subject is human and has one or more cardiovascular diseases.

Combination Therapies

As used herein, the term "co-administer" refers to administration of two or more therapies or two or more therapeutic agents (e.g., one or more compounds and an additional therapy; or a compound disclosed herein for inhibiting the expression or function of Peptidyl Argininedeiminase (PAD), and an additional therapy) within a 24-hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. For example, when one or more compounds and an additional therapy are administered in different pharmaceutical compositions or at different times, routes of administration can be same or different. For example, in some embodiments when the PAD inhibitor for inhibiting the expression or function of Peptidyl Argininedeiminase (PAD), and an additional therapy are administered in different pharmaceutical compositions or at different times, routes of administration can be same or different. In some embodiments, the one or more compounds, and the additional therapies are administered sequentially or simultaneously. In some embodiments, the compound is one or more PAD inhibitors.

In some embodiments, the additional therapy is an additional cardiovascular disease therapy. Non-limiting examples of additional therapies include a cholesterol-lowering agent, glucose-lowering agent, lipid-lowering agent, fat/adipose tissue mass-lowering agent, blood pressure lowering agent, dietary therapy, physical therapy, behavior therapy, surgery, drug therapy, or a combination thereof. In some embodiments, the additional therapies are a cholesterol-lowering agent, glucose-lowering agent, lipid-lowering agent, fat/adipose tissue mass-lowering agent, blood pressure lowering agent, dietary therapy, physical therapy, behavior therapy, surgery, drug therapy, or any combination thereof.

Pharmaceutical Compositions

In various embodiments, the present invention provides a pharmaceutical composition comprising one or more PAD inhibitors; and a pharmaceutically acceptable excipient or carrier.

For administration to a subject, the one or more compounds for treating one or more diseases can be provided in pharmaceutical acceptable compositions. These pharmaceutically acceptable compositions comprise one or more compounds formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, contents of all of which are herein incorporated by reference. In some embodiments, the compound is one or more PAD inhibitors.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the composition. In some embodiments a liquid formulation may be used. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %. In some embodiments the sugar or sugar alcohol concentration is between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

In some embodiments a buffer is used in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

A "pharmaceutically acceptable salt", as used herein, is intended to encompass any compound described herein that is utilized in the form of a salt thereof, especially where the salt confers on the compound improved pharmacokinetic properties as compared to the free form of the compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-"hydroxyethane-sulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

The term "prodrug" as used herein refers to compounds that can be converted via some chemical or physiological process (e.g., enzymatic processes and metabolic hydrolysis) to a compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which are herein incorporated by reference in its entirety.

Kits

In various embodiments, the present invention provides a kit for treating cardiovascular disease. The kit comprises one or more compounds to treat cardiovascular disease in the subject and instructions for use. In some embodiments, the compound is one or more PAD inhibitors.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat cardiovascular disease. Optionally, the kit also contains other useful components, such as, measuring tools, diluents, buffers, pharmaceutical compositions, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, for example to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In various embodiments, the present invention provides a kit for obtaining a biomarker signature for a subject, wherein the biomarker signature comprises one or more citrullinated proteins, one or more citrullinated peptides, or one or more PAD isoforms, the kit comprising: reagents and instructions for sample processing and preparation; and instructions for using the kit to obtain the biomarker signature for the subject. In some embodiments, the kit further comprises an internal standard.

In various embodiments, the present invention provides a kit for identifying and/or assessing a cardiovascular disease in a subject, the kit comprising: reagents and instructions for sample processing and preparation; and instructions for using the kit to obtain the biomarker signature for the subject, wherein the biomarker signature comprises one or more citrullinated proteins, one or more citrullinated peptides, or one or more PAD isoforms; a plurality of reference biomarker signatures characteristic for cardiovascular disease; and instructions for using the kit to identify and/or assess the cardiovascular disease in the subject. In some embodiments the kit further comprises an internal standard. In some embodiments the plurality of reference biomarker signatures are from a plurality of subjects having one or more cardiovascular diseases. In some embodiments, the plurality of reference biomarker signatures are from a plurality of healthy subjects.

In various embodiments, the present invention provides a kit for identifying and/or assessing a risk of developing cardiovascular disease in a subject, the kit comprising: reagents and instructions for sample processing and preparation; and instructions for using the kit to obtain the biomarker signature for the subject, wherein the biomarker signature comprises one or more citrullinated proteins, one or more citrullinated peptides, or one or more PAD isoforms; a plurality of reference biomarker signatures characteristic for cardiovascular disease; and instructions for using the kit to identify and/or assess the risk of developing cardiovascular disease in the subject. In some embodiments the kit further comprises an internal standard. In some embodiments the plurality of reference biomarker signatures are from a plurality of subjects having one or more cardiovascular diseases. In some embodiments, the plurality of reference biomarker signatures are from a plurality of healthy subjects.

Screening Methods

In various embodiments, the present invention provides a method for identifying an inhibitor of one or more peptidylarginine deiminase isoforms (PAD isoforms), comprising: contacting a sample with a molecule of interest, wherein the sample comprises one or more peptidylarginine deiminase isoforms (PAD isoforms); and determining whether the contact results in decreased expression of the peptidylarginine deiminase isoform (PAD isoform), wherein a decrease in expression of the peptidylarginine deiminase isoform (PAD isoform) indicates that the molecule of interest is an inhibitor of the peptidylarginine deiminase isoform (PAD isoform).

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Tissue Samples: Human Left ventricular (LV) transmural tissue samples were obtained from patients with end-stage ISHD, IDCM and non-failing donor hearts. The tissue from these deidentified tissue banked samples was collected in cardioplegic solution and stored in liquid nitrogen. The samples were provided to us by Dr. Cris Dos Remoidois, University of Sidney, Australia. A subset is analyzed in this study (Table 2).

TABLE 2

Characteristic of HF Samples

| Code # | Type | ID # | Sex | Age | LVEF (%) |
|---|---|---|---|---|---|
| 1 | ISHD | 3.062 | M | 31 | 23 |
| 2 | ISHD | 3.007 | M | 45 | — |
| 3 | ISHD | 2.063 | M | 46 | 25 |
| 4 | ISHD | 3.123 | M | 47 | 20 |
| 5 | ISHD | 3.078 | M | 50 | — |
| 6 | ISHD | 3.106 | M | 52 | — |
| 7 | ISHD | 3.105 | M | 54 | — |
| 8 | ISHD | 3.143 | M | 54 | — |
| 9 | ISHD | 3.075 | F | 43 | — |
| 10 | ISHD | 3.103 | F | 49 | — |
| 11 | IDCM | 2.092 | M | 43 | — |
| 12 | IDCM | 3.104 | M | 46 | — |
| 13 | IDCM | 3.138 | M | 56 | 15 |
| 14 | IDCM | 2.095 | M | 57 | 10 |
| 15 | IDCM | 4.098 | M | 58 | 20 |
| 16 | IDCM | 4.058 | M | 60 | 15 |
| 17 | IDCM | 3.096 | F | 23 | 15 |
| 18 | IDCM | 3.159 | F | 31 | 20 |
| 19 | IDCM | 2.111 | F | 53 | 20 |
| 20 | IDCM | 2.115 | F | 54 | 22 |
| 21 | Donor | 4.015 | M | 19 | — |
| 22 | Donor | 2.152 | M | 23 | — |

TABLE 2-continued

Characteristic of HF Samples

| Code # | Type | ID # | Sex | Age | LVEF (%) |
|---|---|---|---|---|---|
| 23 | Donor | 4.013 | M | 23 | — |
| 24 | Donor | 3.135 | M | 26 | — |
| 25 | Donor | 3.145 | M | 39 | — |
| 26 | Donor | 2.149 | M | 44 | — |
| 27 | Donor | 3.141 | M | 52 | — |
| 28 | Donor | 3.084 | F | 27 | — |
| 29 | Donor | 3.073 | F | 41 | — |
| 30 | Donor | 3.056 | F | 45 | — |

Subfractionation of Heart Tissue: The method produces three fractions based on solubility at different pHs: (1) cytoplasmic-enriched extract (neutral pH), (2) myofilament-enriched extract (acidic pH), and (3) membrane protein-enriched pellet. Fractionation of heart tissue in this manner provides the basis for in-depth proteomic analysis (Kane et al., *Cardiovascular Proteomics* 2007, 357:87-90).

Targeted analysis of protein citrullination by mass spectrometry: MS has become the method of choice for the analysis of PTMs on proteins and peptides. However, PTMs are typically present in relatively small amounts in heterogeneous and complex protein mixtures. Specifically, in the case of citrullination, the identification is complicated by the fact that the mass shift resulting from the conversion of arginine to citrulline is small (+1 Da), making it difficult to identify the citrullination using low-resolution MS instrumentation. To overcome this challenge, we used an LTQ Orbitrap high-resolution MS (Stensland et al., *Rapid Commun Mass Spectrom* 2009, 23:2754-2762). Also, as this derivatization strategy adds a specific mass tag of ±239 Da (FIG. 1A) to the citrulline reside, we are able to confidently identify the site of modification. Our recent investigations show that by using this strategy, we can identify citrullinated peptides from a heterogeneous mixture such as a tryptic digest of bovine serum albumin (BSA) (FIG. 1B).

Two-dimensional gel electrophoresis: Two-dimensional gel electrophoresis (2DE) was performed on immobilized pH gradient 18-cm strips (GE Healthcare, Buckinghamshire, UK), pH ranges 4 to 7 in the first dimension. The sample was re-suspended in 2-DE lysis buffer containing 4% w/v CHAPS, 7 M urea, 2 M thiourea, 10 mM Tris-HCl, pH 8.3 and 1 mM EDTA. Before performing 2D-DIGE, protein samples were labeled with N-hydroxy succinimidyl ester-derivatives of the cyanine dyes Cy2, Cy3 and Cy5. Briefly, 150 µg of protein sample was minimally labeled with 375 pmol of either Cy3 or Cy5 for comparison on the same 2-DE. To facilitate image matching and cross-gel statistical comparison, a pool of all samples was also prepared and labeled with Cy2 at a molar ratio of 2.5 pmol Cy2 per µg of protein as an internal standard for all gels. Thus, the triplicate samples and the internal standard could be run and quantify on multiple 2-DE. The labeling reactions were performed in the dark on ice for 30 min and then quenched with a 20-fold molar ratio excess of free L-lysine for 10 min. The differentially Cy3- and Cy5-labeled samples were then mixed with the Cy2-labeled internal standard and reduced with dithiothreitol for 30 min. IPG buffer, pH 4-7 nonlinear (2% (v/v), GE Healthcare) was added and the final volume was adjusted to 350 µl with 2D-lysis buffer for rehydration. Immobilized pH gradient (IPG) Strips (18 cm pH 4-7 linear gradients) were actively rehydrated with the sample (150 µg of protein in 350 µL IEF buffer) at 50 V for 12 hrs, followed by a rapid voltage ramping consisting of 1 hr each at 250, 500, and 1000 V, followed by 10000 V for 45 kVh at 20° C. Isoelectric focusing was performed a total of 62.5 kV-h at 20° C. Strips were equilibrated in 6 M urea, 30% (v/v) glycerol, 4% SDS (w/v), 100 mM Tris-HCl (pH8.8), 65 mM dithiothreitol for 20 min and then in the same buffer containing 240 mM iodoacetamide for another 20 min. The equilibrated IPG strips were transferred onto 20×20-cm 10% polyacrylamide gels. Gels were run overnight on a Protean® II XL system (Bio-Rad) at 90 V with 2(n-morpholino) ethansulfonic acid (MES) running buffer. Gels were subsequently scanned using a Typhoon variable mode imager 9210 (GE Healthcare). The majority of spots visible with CyDye staining are usually visible with silver staining, according to the protocol of Shevchenko et al. (*Anal Chem* 1996, 68:850-858).

In-gel digestion and peptide extraction: Upon completion of gel staining, individual bands were excised from the gel. In-gel digestion and peptide extraction was achieved using the improved protocol previously (Zhang et al., *J Proteome Res* 2007, 6:2295-2303). Briefly, cTnI bands were excised, cut into 1 mm³ pieces, and washed 3 times with 50% acetonitrile/25 mM ammonium bicarbonate for 15 min with shaking. Gel pieces were incubated with 25 mM ammonium bicarbonate+10 mM dithiothreitol for 60 min at 55° C., washed with acetonitrile (ACN), then incubated with 20 mM ammonium bicarbonate+55 mM iodoacetamide (freshly made) for 30 minutes in the dark. The gel pieces were washed with acetonitrile, air dried, and rehydrated with 12.5 ng/µL trypsin (Promega, sequencing grade, Madison, Wis.) in 25 mM ammonium bicarbonate, then incubated at 37° C. for 18 hr or overnight. The liquid was transferred to a clean tube. Peptides were extracted twice using 50% ACN+0.1 TFA % for 20 min at 25° C., followed by 20 min of shaking, 1 min of centrifugation, and combined two times of extraction with the liquid from the previous step.

Immunoblotting analysis: Protein samples were dissolved in Laemmli buffer (50 mM TrisHCl, pH 6.8, 2% SDS, 10% glycerol, bromophenol blue) with 5% β-mercapto-ethanol and incubated at 95° C. for five minutes. The samples were loaded on a 10% TrisHCl polyacrylamidegel (Biorad, Hercules, Calif., USA) and electrophoresis was performed by applying 150 V for 70 minutes. After SDS-PAGE, separated proteins from mouse were blotted to nitrocellulose membrane (Millipore, USA). The transfer was carried out in a buffer containing 25 mM Tris, 192 mM glycine and 10% volume fraction of methanol, pH=8.3 at a constant voltage setting of 100 V for 60 min in a cell for electrophoretic transfer. The presence of citrullinated proteins on the nitrocellulose blots was detected using the anti-modified citrulline (AMC) detection kit (Upstate, Charlottesville, Va., USA) according to the manufacturer's protocol.

Detection of citrullinated protein in situ: Immunostaining of citrullinated proteins was performed by using anti-modified citrulline IgG polyclonal antibody. Briefly, slides for citrullination staining were modified in a strong acid solution containing antipyrine and 2,3-butanedoine for 3 hours at 37° C. Endogenous peroxidase activity was blocked by incubation in 0.3% $H_2O_2$ in methanol for 18 minutes. Non-specific protein activity was blocked by incubation with a non-serum protein solution (DAKO Corporation, Carpinteria, Calif.). Scoring for the citrulline staining was also performed blinded using 5-point scale (1-3 in 0.5 increments) corresponding to minimal, moderate and marked citrullination stains.

Results: Our data indicate that citrullination occurs in the myocardium. We have detected citrullinated protein in healthy like diseases samples. Similar, we found modified protein in each exanimate fractions. Interesting we have found a few citrullinated residue in myosin and tropomyosin which are the molecular motor that drives sarcomere shortening through a cyclic, ratchet-like interaction with actin. Therefore, it appears that citrullination of myocardial proteins may influence cardiac performance in heart failure.

In vivo targeted analysis of protein citrullination by tandem mass spectrometry: We investigated the 2,3-butanedione and antipyrine modification for specific detection and identification of citrulline-containing peptides by tandem MS/MS. Under the conditions applied, the modification by 2,3-butanedione/antipyrine is absolutely specific for citrulline. Under this condition we were able to identify several proteins in untreated subcellular fractions of human myocardium (Tables 1A and 1B). Interestingly, some modified sites seem to be more specific for HF vs. control (FIG. 1A-FIG. 1B).

Figure 2:
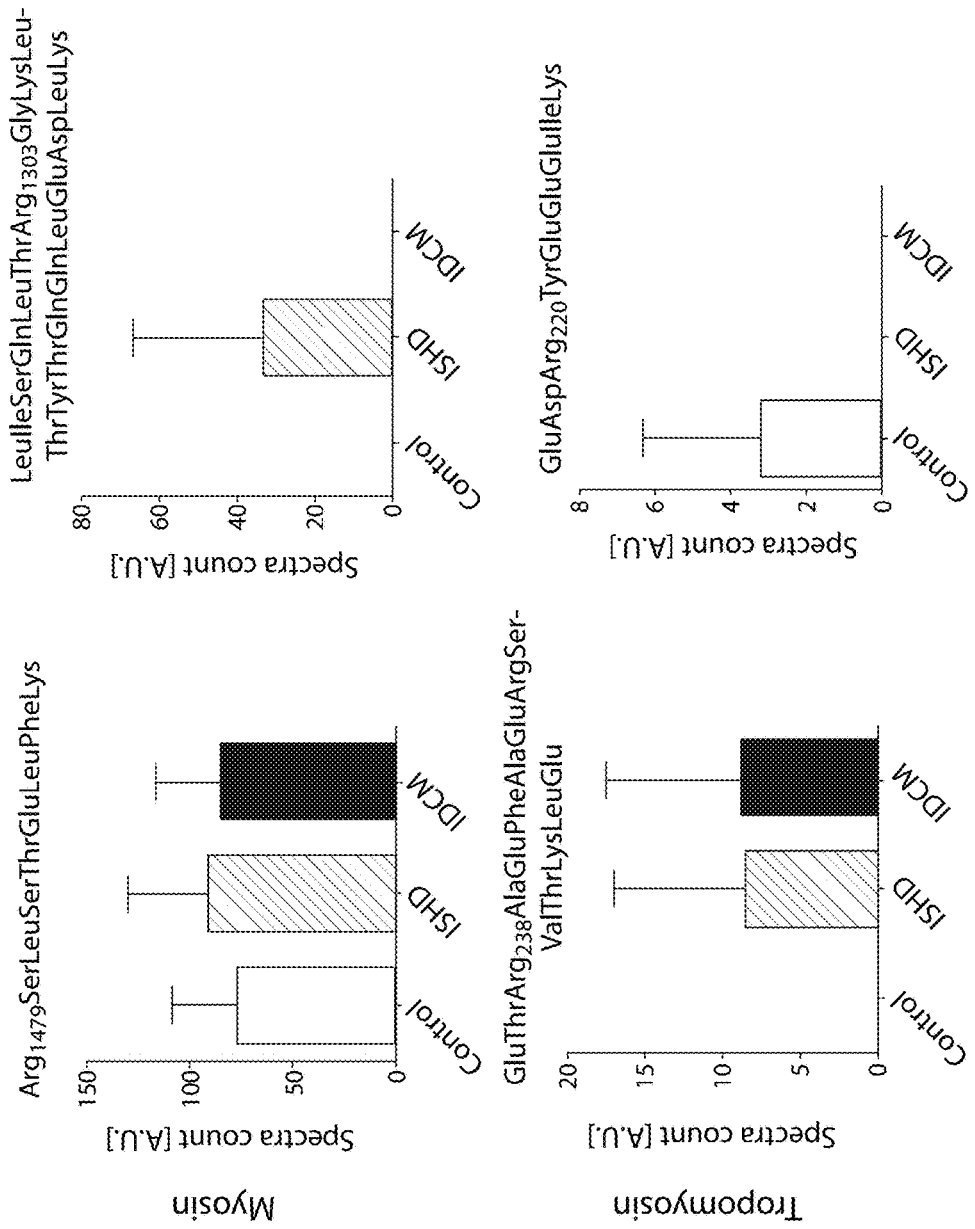

Citrullination occurs in human heart tissue: To support our hypothesis, we have examined human heart tissue for the presence of citrullinated proteins. Using a commercially available antibody (Anti-Citruline (modified) Detection Kit, Millipore) to citrullinated proteins, we have verified that citrullinated proteins are present in human heart tissue (FIG. 2A). Furthermore, we use immunohistochemistry to localize citrullination in heart tissue (FIG. 2B). As shown in FIG. 2A two main proteins, myosin and actin act differently in compared groups. In HF tissue, a significant increase of myosin heavy chain citrullination vs. control was seen. On the other hand, actin showed opposite pattern to myosin. Additional the IHC staining of control heart tissue proved occurrence of citrullinated proteins in human heart tissue.

Example 2

Methods: Adult male mice (C57BL6) were subjected to either transverse aortic constriction (TAC, n=8) or a sham operation (n=3) for 10 days, and the PAD inhibitor, Cl-amidine dissolved in DMSO (20 mg/kg or DMSO or control saline) were administered by every other day by intraperitoneal injection (150 ul) (FIG. 6). TAC-induced cardiac hypertrophy was assessed by heart weight, hematoxylin-eosin, and picrosirius red staining to determine the myocyte fibrosis and collagen deposition, western blot (WB) and mass spectrometry (MS) was used to assess protein expression and citrullination (FIG. 7A-FIG. 7C).

Results: Cl-amidine treatment improved cardiac function by significantly reduced fibrosis and tissue loss following injury (heart weight to body weight ratio:$p=0.027$; $p=0.013$; $p=0.029$ by Student's t test) (FIG. 7B) and by significantly lower expression of TGFβ ($p=0.05$, $p=0.016$) (FIG. 8D), Smad2 ($p=0.018$, $p=0.033$) (FIG. 8B), Smad4 ($p=0.021$) (FIG. 8A), and Vimentin ($p=0.013$; $p=0.029$) (FIG. 8C) in the post-surgery mice.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

We claim:

1. A method for diagnosing and treating cardiovascular disease in a subject, comprising:
   obtaining a sample from the subject, wherein the sample is selected from the group consisting of heart tissue, blood, plasma, and serum; and wherein the subject is human;
   detecting an amount of one or more citrullinated proteins in the sample from the subject;
   comparing the amount of the citrullinated proteins in the sample from the subject to an amount of one or more citrullinated proteins from a reference sample, wherein a change in the amount of the citrullinated proteins in the sample from the subject relative to the amount of the citrullinated proteins from the reference sample is a diagnosis of cardiovascular disease in the subject,
   wherein the cardiovascular disease is selected from the group consisting of heart failure, ischemic heart disease (ISHD), and idiopathic dilated cardiomyopathy (IDCM); wherein the citrullinated proteins are selected from the group consisting of myosin heavy chain, myosin binding protein C, tropomyosin α1, tropomyosin 3, actin, lipoprotein lipase, sulfhydryl oxidase 2, putative zinc finger protein 818, disintegrin and metalloproteinase domain-containing protein 10, titin, Zinc finger ZZ-type and EF-hand domain-containing protein 1, serpin, and tRNA-dihydrouridine synthase; and wherein the citrullinated proteins comprise an amino acid sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34; and
   administering a treatment to the subject based on the diagnosis, wherein the treatment comprises a therapeutically effective amount of one or more PAD inhibitors.

2. The method of claim 1, wherein the amount of the citrullinated proteins is detected using mass spectrometry, high resolution mass spectrometry, tandem mass spectrometry, binding assay, immunoassay, antibody binding or immunohistochemistry.

3. The method of claim 1, wherein the method further comprises administering one or more additional therapies to the subject.

4. The method of claim 3, wherein the additional therapies are selected from the group consisting of cholesterol-lowering agent, glucose-lowering agent, lipid-lowering agent, fat/adipose tissue mass-lowering agent, blood pressure lowering agent, dietary therapy, physical therapy, behavior therapy, surgery, drug therapy, and any combination thereof.

5. The method of claim 1, wherein the PAD inhibitors are selected from the group consisting of F-amidine [N-α-benzoyl-N5-(2-fluoro-1-iminoethyl)-1-ornithine amide], 2-chloroacetamidine, Cl-amidine [N-α-benzoyl-N5-(2-chloro-1-iminoethyl)-1-ornithine amide], o-F-amidine [N-α-(2-carboxyl)benzoyl-N5-(2-fluoro-1-iminoethyl)-L-ornithine amide], o-Cl-amidine [N α-(2-carboxyl)benzoyl-N5-(2-Chloro-1-iminoethyl)-L-ornithine amide], TDF tripeptide (Thr-Asp-F-amidine), and any combination thereof.

6. The method of claim 1, wherein the therapeutically effective amount of the PAD inhibitors is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

7. The method of claim 1, wherein the PAD inhibitors are administered to the subject 1-3 times per day or 1-7 times per week.

8. The method of claim 1, wherein the PAD inhibitors are administrated to the subject for 1-5 days, 1-5 weeks, 1-5 months, or 1-5 years.

9. The method of claim 3, wherein the PAD inhibitors and the additional therapies are administered sequentially or simultaneously.

10. A method for treating cardiovascular disease in a subject in whom a change in an amount of one or more citrullinated proteins has been detected relative to an amount of one or more citrullinated proteins in a reference sample, comprising:
providing a subject diagnosed with cardiovascular disease in whom a change in an amount of one or more citrullinated proteins has been detected relative to an amount of one or more citrullinated proteins in a reference sample, wherein the subject is human; wherein the cardiovascular disease is selected from the group consisting of heart failure, ischemic heart disease (ISHD), and idiopathic dilated cardiomyopathy (IDCM); wherein the citrullinated proteins are selected from the group consisting of myosin heavy chain, myosin binding protein C, tropomyosin α1, tropomyosin 3, actin, lipoprotein lipase, sulfhydryl oxidase 2, putative zinc finger protein 818, disintegrin and metalloproteinase domain-containing protein 10, titin, Zinc finger ZZ-type and EF-hand domain-containing protein 1, serpin, and tRNA-dihydrouridine synthase; and wherein the citrullinated proteins comprise an amino acid sequence selected from the group consisting of SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34; and
administering a treatment to the subject, wherein the treatment comprises a therapeutically effective amount of one or more PAD inhibitors.

11. The method of claim 10, wherein the method further comprises administering one or more additional therapies to the subject.

12. The method of claim 11, wherein the additional therapies are selected from the group consisting of cholesterol-lowering agent, glucose-lowering agent, lipid-lowering agent, fat/adipose tissue mass-lowering agent, blood pressure lowering agent, dietary therapy, physical therapy, behavior therapy, surgery, drug therapy, and any combination thereof.

13. The method of claim 10, wherein the PAD inhibitors are selected from the group consisting of F-amidine [N-α-benzoyl-N5-(2-fluoro-1-iminoethyl)-1-ornithine amide], 2-chloroacetamidine, Cl-amidine [N-α-benzoyl-N5-(2-chloro-1-iminoethyl)-1-ornithine amide], o-F-amidine [N-α-(2-carboxyl)benzoyl-N5-(2-fluoro-1-iminoethyl)-L-ornithine amide], o-Cl-amidine [N α-(2-carboxyl)benzoyl-N5-(2-Chloro-1-iminoethyl)-L-ornithine amide], TDF tripeptide (Thr-Asp-F-amidine), and any combination thereof.

14. The method of claim 10, wherein the therapeutically effective amount of the PAD inhibitors is about 0.1 to 0.5 mg/kg/day, 0.5 to 5 mg/kg/day, 5 to 10 mg/kg/day, 10 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day or 900 to 1000 mg/kg/day.

15. The method of claim 10, wherein the PAD inhibitors are administered to the subject 1-3 times per day or 1-7 times per week.

16. The method of claim 10, wherein the PAD inhibitors are administrated to the subject for 1-5 days, 1-5 weeks, 1-5 months, or 1-5 years.

17. The method of claim 11, wherein the PAD inhibitors and the additional therapies are administered sequentially or simultaneously.

18. The method of claim 10, wherein the amount of the citrullinated proteins has been detected using mass spectrometry, high resolution mass spectrometry, tandem mass spectrometry, binding assay, immunoassay, antibody binding or immunohistochemistry.

19. The method of claim 1, wherein the reference sample is obtained from a control subject, wherein the control subject does not have the cardiovascular disease.

20. The method of claim 10, wherein the reference sample is obtained from a control subject, wherein the control subject does not have the cardiovascular disease.

* * * * *

```
                          SEQUENCE LISTING

<160> NUMBER OF SEQ ID NOS: 34

<210> SEQ ID NO 1
<211> LENGTH: 9
<212> TYPE: PRT
<213> ORGANISM: Homo sapiens

<400> SEQUENCE: 1

Arg Ser Leu Ser Thr Glu Leu Phe Lys
1               5

<210> SEQ ID NO 2
<211> LENGTH: 19
<212> TYPE: PRT
<213> ORGANISM: Homo sapiens

<400> SEQUENCE: 2

Arg Asp Leu Glu Glu Ala Thr Leu Gln His Glu Ala Thr Ala Ala Ala
1               5                   10                  15

Leu Arg Lys

<210> SEQ ID NO 3
<211> LENGTH: 17
<212> TYPE: PRT
<213> ORGANISM: Homo sapiens

<400> SEQUENCE: 3

His Arg Leu Gln Asn Glu Ile Glu Asp Leu Met Val Asp Val Glu Arg
1               5                   10                  15

Ser

<210> SEQ ID NO 4
<211> LENGTH: 15
<212> TYPE: PRT
<213> ORGANISM: Homo sapiens

<400> SEQUENCE: 4

Lys Lys Leu Ala Gln Arg Leu Gln Glu Ala Glu Glu His Val Glu
1               5                   10                  15

<210> SEQ ID NO 5
<211> LENGTH: 20
<212> TYPE: PRT
<213> ORGANISM: Homo sapiens

<400> SEQUENCE: 5

Arg Pro Ala Pro Asp Ala Pro Glu Asp Thr Gly Asp Ser Asp Glu Trp
1               5                   10                  15

Val Phe Asp Lys
```

<210> SEQ ID NO 6
<211> LENGTH: 9
<212> TYPE: PRT
<213> ORGANISM: Homo sapiens

<400> SEQUENCE: 6

Glu Asp Arg Tyr Glu Glu Glu Ile Lys
1               5

<210> SEQ ID NO 7
<211> LENGTH: 16
<212> TYPE: PRT
<213> ORGANISM: Homo sapiens

<400> SEQUENCE: 7

Glu Thr Arg Ala Glu Phe Ala Glu Arg Ser Val Thr Lys Leu Glu Lys
1               5                   10                  15

<210> SEQ ID NO 8
<211> LENGTH: 14
<212> TYPE: PRT
<213> ORGANISM: Homo sapiens

<400> SEQUENCE: 8

Ala Glu Glu Ala Asp Arg Lys Tyr Glu Glu Val Ala Arg Lys
1               5                   10

<210> SEQ ID NO 9
<211> LENGTH: 23
<212> TYPE: PRT
<213> ORGANISM: Homo sapiens

<400> SEQUENCE: 9

Ala Gly Phe Ala Gly Asp Asp Ala Pro Arg Ala Val Phe Pro Ser Ile
1               5                   10                  15

Val Gly Arg Pro Arg His Gln
            20

<210> SEQ ID NO 10
<211> LENGTH: 10
<212> TYPE: PRT
<213> ORGANISM: Homo sapiens

<400> SEQUENCE: 10

Val Asn Ser Arg Pro Ile Lys Asp Leu Lys
1               5                   10

<210> SEQ ID NO 11
<211> LENGTH: 11
<212> TYPE: PRT
<213> ORGANISM: Homo sapiens

<400> SEQUENCE: 11

Tyr Arg Ile Gln Glu Phe Lys Gly Gly Tyr His
1               5                   10

<210> SEQ ID NO 12
<211> LENGTH: 16
<212> TYPE: PRT
<213> ORGANISM: Homo sapiens

<400> SEQUENCE: 12

Asp Ile Leu Ile Pro Pro Glu Gly Glu Leu Asp Ala Asp Leu Arg Lys
1               5                   10                  15

<210> SEQ ID NO 13
<211> LENGTH: 15
<212> TYPE: PRT
<213> ORGANISM: Homo sapiens

<400> SEQUENCE: 13

Val Ile Ala Glu Arg Gly Leu Gly Asp Val Asp Gln Leu Val Lys
1               5                   10                  15

<210> SEQ ID NO 14
<211> LENGTH: 20
<212> TYPE: PRT
<213> ORGANISM: Homo sapiens

<400> SEQUENCE: 14

Ile Val Val Val Thr Ala Gly Val Arg Gln Gln Glu Gly Glu Ser Arg
1               5                   10                  15

Leu Asn Leu Val
            20

<210> SEQ ID NO 15
<211> LENGTH: 22
<212> TYPE: PRT
<213> ORGANISM: Homo sapiens

<400> SEQUENCE: 15

Arg Leu Tyr Gly Ser Glu Ala Phe Ala Thr Asp Phe Gln Asp Ser Ala
1               5                   10                  15

Ala Ala Lys Lys Leu Ile
            20

<210> SEQ ID NO 16
<211> LENGTH: 14
<212> TYPE: PRT
<213> ORGANISM: Homo sapiens

<400> SEQUENCE: 16

Ser Arg Asp Leu Gln Leu Ala Val Asp Gln Leu Lys Leu Lys
1               5                   10

<210> SEQ ID NO 17
<211> LENGTH: 13
<212> TYPE: PRT
<213> ORGANISM: Homo sapiens

<400> SEQUENCE: 17

Lys Leu Asp Pro Leu Glu Gly Leu Asp Glu Pro Thr Arg
1               5                   10

<210> SEQ ID NO 18
<211> LENGTH: 23
<212> TYPE: PRT
<213> ORGANISM: Homo sapiens

<400> SEQUENCE: 18

Arg Gln Pro Pro Ala Ala Leu Ala Lys Pro Pro Gly Thr Pro Pro Ser
1               5                   10                  15

Leu Gly Ala Ser Pro Ala Lys
            20

-continued

```
<210> SEQ ID NO 19
<211> LENGTH: 9
<212> TYPE: PRT
<213> ORGANISM: Homo sapiens

<400> SEQUENCE: 19

Arg Ser Leu Ser Thr Glu Leu Phe Lys
1               5

<210> SEQ ID NO 20
<211> LENGTH: 20
<212> TYPE: PRT
<213> ORGANISM: Homo sapiens

<400> SEQUENCE: 20

Leu Ile Ser Gln Leu Thr Arg Gly Lys Leu Thr Tyr Thr Gln Gln Leu
1               5                   10                  15

Glu Asp Leu Lys
            20

<210> SEQ ID NO 21
<211> LENGTH: 16
<212> TYPE: PRT
<213> ORGANISM: Homo sapiens

<400> SEQUENCE: 21

Gln Arg Leu Gln Asp Ser Glu Glu Gln Val Glu Ala Val Asn Ala Lys
1               5                   10                  15

<210> SEQ ID NO 22
<211> LENGTH: 20
<212> TYPE: PRT
<213> ORGANISM: Homo sapiens

<400> SEQUENCE: 22

Arg Pro Ala Pro Asp Ala Pro Glu Asp Thr Gly Asp Ser Asp Glu Trp
1               5                   10                  15

Val Phe Asp Lys
            20

<210> SEQ ID NO 23
<211> LENGTH: 16
<212> TYPE: PRT
<213> ORGANISM: Homo sapiens

<400> SEQUENCE: 23

Glu Thr Arg Ala Glu Phe Ala Glu Arg Ser Val Thr Lys Leu Glu Lys
1               5                   10                  15

<210> SEQ ID NO 24
<211> LENGTH: 24
<212> TYPE: PRT
<213> ORGANISM: Homo sapiens

<400> SEQUENCE: 24

Leu Glu Glu Ala Glu Lys Ala Ala Asp Glu Ser Glu Arg Gly Met Lys
1               5                   10                  15

Val Ile Glu Asn Arg Ala Leu Lys
            20

<210> SEQ ID NO 25
<211> LENGTH: 23
<212> TYPE: PRT
```

```
<400> SEQUENCE: 25

Ala Gly Phe Ala Gly Asp Asp Ala Pro Arg Ala Val Phe Pro Ser Ile
1               5                   10                  15

Val Gly Arg Pro Arg His Gln
            20

<210> SEQ ID NO 26
<211> LENGTH: 15
<212> TYPE: PRT
<213> ORGANISM: Homo sapiens

<400> SEQUENCE: 26

Val Ile Ala Glu Arg Gly Leu Gly Asp Val Asp Gln Leu Val Lys
1               5                   10                  15

<210> SEQ ID NO 27
<211> LENGTH: 9
<212> TYPE: PRT
<213> ORGANISM: Homo sapiens

<400> SEQUENCE: 27

Leu Phe Pro Gly Arg Pro Pro Val Lys
1               5

<210> SEQ ID NO 28
<211> LENGTH: 15
<212> TYPE: PRT
<213> ORGANISM: Homo sapiens

<400> SEQUENCE: 28

Asn Asp Glu Arg Asn Tyr Arg Glu Ile Pro Ala Ile Lys Ile Lys
1               5                   10                  15

<210> SEQ ID NO 29
<211> LENGTH: 21
<212> TYPE: PRT
<213> ORGANISM: Homo sapiens

<400> SEQUENCE: 29

Cys Asp Val Phe Met Arg Cys Arg Leu Val Asp Ala Asp Gly Pro Leu
1               5                   10                  15

Ala Arg Leu Lys Lys
            20

<210> SEQ ID NO 30
<211> LENGTH: 11
<212> TYPE: PRT
<213> ORGANISM: Homo sapiens

<400> SEQUENCE: 30

Tyr Arg Ile Gln Glu Phe Lys Gly Gly Tyr His
1               5                   10

<210> SEQ ID NO 31
<211> LENGTH: 14
<212> TYPE: PRT
<213> ORGANISM: Homo sapiens

<400> SEQUENCE: 31

Leu Ser Gly Val Leu Thr Val Lys Ala Gly Asp Thr Ile Arg
1               5                   10
```

```
<210> SEQ ID NO 32
<211> LENGTH: 13
<212> TYPE: PRT
<213> ORGANISM: Homo sapiens

<400> SEQUENCE: 32

Lys Leu Asp Pro Leu Glu Gly Leu Asp Glu Pro Thr Arg
1               5                   10

<210> SEQ ID NO 33
<211> LENGTH: 21
<212> TYPE: PRT
<213> ORGANISM: Homo sapiens

<400> SEQUENCE: 33

Phe Tyr Gln Thr Ser Val Glu Ser Thr Asp Phe Ala Asn Ala Pro Glu
1               5                   10                  15

Glu Ser Arg Lys Lys
            20

<210> SEQ ID NO 34
<211> LENGTH: 25
<212> TYPE: PRT
<213> ORGANISM: Homo sapiens

<400> SEQUENCE: 34

Gly Gln Glu Lys Thr Cys Arg Glu Thr Glu Val Gly Asp Pro Ala Gly
1               5                   10                  15

Asn Glu Leu Ala Glu Pro Glu Ala Lys
            20                  25
```